(12) United States Patent
Kawagishi et al.

(10) Patent No.: US 10,950,204 B2
(45) Date of Patent: Mar. 16, 2021

(54) DIAGNOSIS SUPPORT APPARATUS AND DIAGNOSIS SUPPORT METHOD

(71) Applicant: CANON KABUSHIKI KAISHA, Tokyo (JP)

(72) Inventors: Masami Kawagishi, Kyoto (JP); Hiroyuki Sekiguchi, Kyoto (JP); Akihito Uji, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 373 days.

(21) Appl. No.: 15/137,084

(22) Filed: Apr. 25, 2016

(65) Prior Publication Data

US 2016/0335394 A1 Nov. 17, 2016

(30) Foreign Application Priority Data

May 14, 2015 (JP) .............................. JP2015-099514

(51) Int. Cl.
  *G09G 5/14* (2006.01)
  *G06F 3/14* (2006.01)
  (Continued)

(52) U.S. Cl.
  CPC .................. *G09G 5/14* (2013.01); *G06F 3/14* (2013.01); *G06T 11/60* (2013.01); *G16H 30/20* (2018.01);
  (Continued)

(58) Field of Classification Search
  CPC ........ G06F 19/321; G06F 19/34; G16H 40/63
  (Continued)

(56) References Cited

U.S. PATENT DOCUMENTS 5,779,634 A * 7/1998 Ema ....................... G06F 19/321
                                                          600/407
2004/0003001 A1* 1/2004 Shimura ........... G06F 17/30259
(Continued)

FOREIGN PATENT DOCUMENTS

JP   2009-039221 A   2/2009
JP   2009-059381     3/2009
(Continued)

OTHER PUBLICATIONS

U.S. Appl. No. 15/097,422, filed Apr. 13, 2016.
(Continued)

*Primary Examiner* — Irete F Ehichioya
*Assistant Examiner* — Ken Hoang
(74) *Attorney, Agent, or Firm* — Venable LLP

(57) ABSTRACT

A diagnosis support apparatus detects a finding and a position, on a diagnosis image as a diagnosis target medical image, which corresponds to the finding from the image, and searches a database storing a plurality of medical images linked to findings and diagnosis names by using the detected finding. The diagnosis support apparatus simultaneously performs or switches between the first display operation of causing a display unit to display the diagnosis image, together with the detected finding and a position on the display which corresponds to the finding and the second display operation of causing the display unit to display the found medical image, together with a diagnosis name associated with the medical image.

27 Claims, 12 Drawing Sheets

(51) Int. Cl.
  *G06T 11/60* (2006.01)
  *G16H 30/20* (2018.01)
  *G16H 40/63* (2018.01)
(52) U.S. Cl.
  CPC ......... *G16H 40/63* (2018.01); *G06T 2200/24* (2013.01); *G09G 2380/08* (2013.01)
(58) Field of Classification Search
  USPC .......................... 702/168, 19, 56; 705/3, 783
  See application file for complete search history.

(56) References Cited

U.S. PATENT DOCUMENTS

| | | | |
|---|---|---|---|
| 2008/0215630 A1* | 9/2008 | Oosawa | G16H 50/70 |
| 2008/0243395 A1* | 10/2008 | Oosawa | G16H 50/70 |
| | | | 702/19 |
| 2010/0274776 A1* | 10/2010 | Iizuka | G06F 17/30247 |
| | | | 707/706 |
| 2011/0199390 A1 | 8/2011 | Iizuka et al. | 345/629 |
| 2011/0213748 A1 | 9/2011 | Kawagishi et al. | 706/52 |
| 2012/0136882 A1 | 5/2012 | Kawagishi et al. | 707/758 |
| 2012/0254101 A1 | 10/2012 | Kawagishi | 706/52 |
| 2013/0006087 A1* | 1/2013 | Kondo | G06F 19/3443 |
| | | | 600/407 |
| 2013/0212056 A1 | 8/2013 | Kawagishi | 706/46 |
| 2014/0055791 A1 | 2/2014 | Iwase et al. | 356/479 |
| 2014/0072193 A1* | 3/2014 | Motomura | G06T 7/0012 |
| | | | 382/128 |
| 2014/0089000 A1* | 3/2014 | Takata | G06F 19/321 |
| | | | 705/2 |
| 2014/0379382 A1* | 12/2014 | Morishima | G06F 19/00 |
| | | | 705/3 |
| 2015/0173684 A1* | 6/2015 | Takata | A61B 5/055 |
| | | | 600/425 |
| 2015/0193908 A1* | 7/2015 | Shim | A61B 8/5292 |
| | | | 345/657 |
| 2016/0267222 A1* | 9/2016 | Larcom | G06F 19/321 |
| 2016/0335394 A1 | 11/2016 | Kawagishi et al. | |

FOREIGN PATENT DOCUMENTS

| | | |
|---|---|---|
| JP | 2010-000133 A | 1/2010 |
| JP | 2014-042650 | 3/2014 |
| JP | 2016-214324 | 12/2016 |

OTHER PUBLICATIONS

K. Nakagomi et al., "Multi-shape graph cuts with neighbor prior constraints and its application to lung segmentation from a chest CT volume", *Medical Image Analysis*, vol. 17(1), pp. 62-77 (Sep. 23, 2012).

M.T. Gurcan et al., "Lung nodule detection on thoracic computed tomography images: preliminary evaluation of a computer-aided diagnosis system", *Medical Physics*, vol. 29(11), pp. 2552-2558 (Oct. 23, 2002).

\* cited by examiner

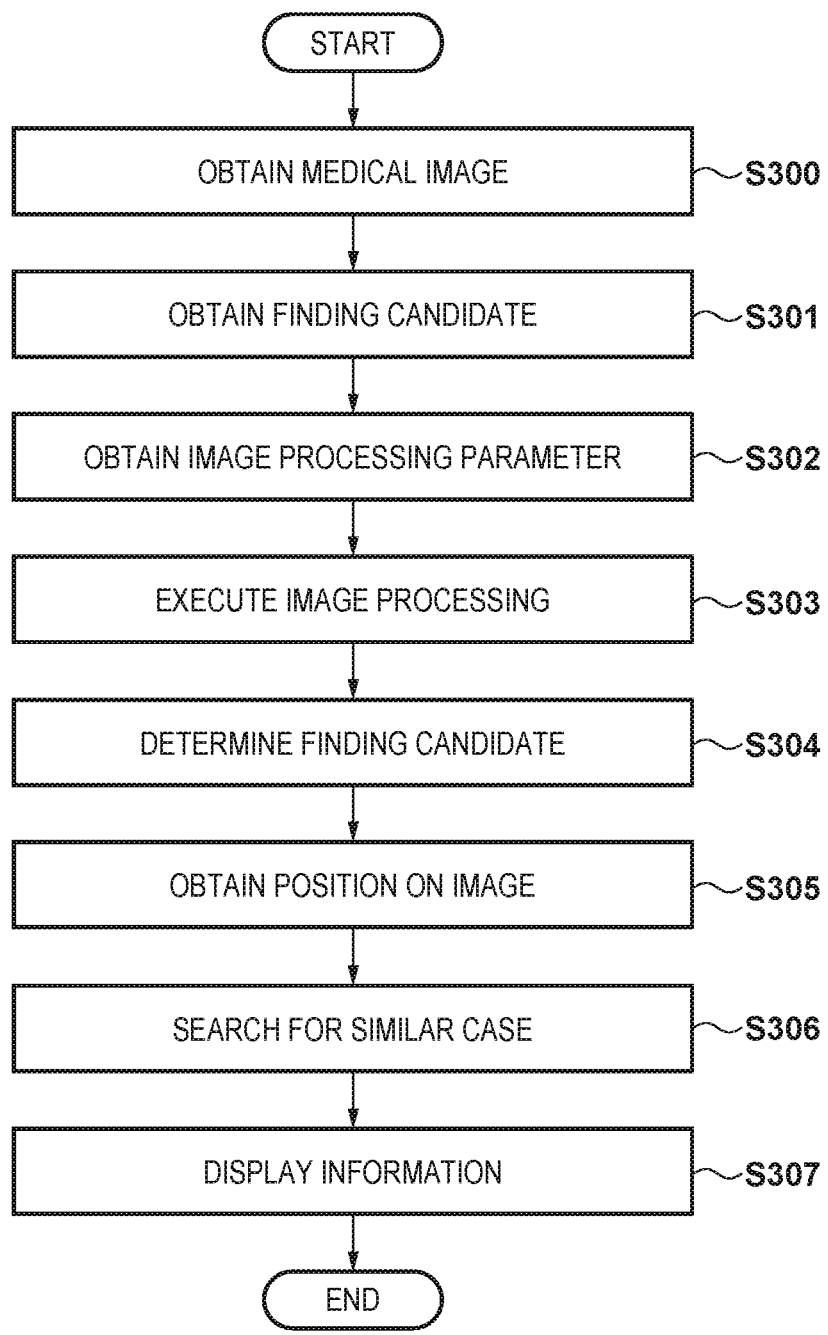

| REGION | IMAGE TYPE | FINDING CANDIDATE |
|---|---|---|
| RETINA | OCT IMAGE | CENTRAL FOVEA CYST-LIKE HOLE |
| | | FIBROUS CYST-LIKE HOLE |
| | | ... |
| | | MACULAR HOLE |
| CHEST REGION | SIMPLE X-RAY | AIR BRONCHOGRAM |
| | | ... |
| | CT | AIR BRONCHOGRAM |
| | | FINE SPICULATION |
| | | ... |
| | | CALCIFICATION |
| | ... | ... |

FIG. 4B

| FINDING CANDIDATE | IMAGE TYPE | IMAGE PROCESSING PARAMETER | DETERMINATION CRITERION |
|---|---|---|---|
| CENTRAL FOVEA CYST-LIKE HOLE | OCT IMAGE | EXTRACT X: 40% - 60%, Z: 30% - 70%, PIXEL VALUE: 10 OR LESS | |
| FIBROUS CYST-LIKE HOLE | OCT IMAGE | EXTRACT X: 25% - 75%, Z: 30% - 70%, PIXEL VALUE: 10 OR LESS | |
| POSTERIOR VITREOUS DETACHMENT | OCT IMAGE | Z: RANGE ABOVE ILM, THINNING | |
| ... | | | |
| MACULAR HOLE | OCT IMAGE | X: 40% - 60%, Z: PIXELS IN CONTACT WITH RPE, PIXEL VALUE: 10 OR LESS, REGION EXPANSION | |
| | FUNDUS IMAGE | PIXEL VALUE: G COMPONENT: 35 OR LESS, RING FILTER (R = 5) | |
| ... | | | |
| SERRATED PERIPHERY | CT IMAGE | FOR NODULAR OPACITY, CALCULATE DISTANCE FROM BARYCENTRIC POSITION TO PERIPHERY (ANGULAR INTERVALS OF π/180) | |
| CALCIFICATION | CT IMAGE | FOR NODULAR OPACITY, EXTRACT CT VALUE: 200 HU OR MORE | |
| ... | | | |

| ID | IMAGING DATE | DIAGNOSIS NAME | FINDING | IMAGE TYPE | MEDICAL IMAGE |
|---|---|---|---|---|---|
| 02345 | 2014/ 12/15 | IDIOPATHIC MACULAR HOLE | MACULAR HOLE, ... | OCT IMAGE | IMAGE DATA |
| ... | ... | ... | ... | ... | ... |

| ID | IMAGING DATE | DIAGNOSIS NAME | FINDING | IMAGE TYPE | MEDICAL IMAGE | |
|---|---|---|---|---|---|---|
| 02345 | 2014/ 12/15 | IDIOPATHIC MACULAR HOLE | MACULAR HOLE, ... | OCT: H SCAN | OCT IMAGE | FUNDUS IMAGE |
| | | | | OCT: V SCAN | OCT IMAGE | |
| ... | ... | ... | ... | ... | ... | |

FIG. 7

CROSS SCAN

RADIAL SCAN

1100 CASE INFORMATION
Name: Satoh Jiro
ID: 30001
Date: 2015/02/04

1110 TARGET CASE (ID: 30001)
1114

1115
SMOOTHNESS (STRONG)
Solid
CALCIFICATION (WEAK)
CLINICAL HISTORY (NONE)

1130 SIMILAR CASE (ID: 21339)
BENIGN NODE — 1132
1134

1135
SMOOTHNESS (STRONG)
Solid
CALCIFICATION (FAINT)
CLINICAL HISTORY (NONE)

1120 SIMILAR CASE LIST

| ID | IMAGING DATE | DIAGNOSIS NAME |
|---|---|---|
| 21339 | 2014/10/27 | BENIGN NODE |
| 29014 | 2015/01/12 | BENIGN NODE |
| 26315 | 2014/05/17 | LUNG CANCER SUSPECTED |
| 25415 | 2015/03/21 | BENIGN NODE |
| 20129 | 2012/04/24 | BENIGN NODE |
| 22428 | 2014/12/14 | METASTATIC LUNG CANCER |
| 21719 | 2012/06/24 | LUNG CANCER |
| 24923 | 2013/12/09 | BENIGN NODE |
| 27716 | 2014/07/15 | BENIGN NODE |

DIAGNOSIS SUPPORT APPARATUS AND DIAGNOSIS SUPPORT METHOD

BACKGROUND OF THE INVENTION

Field of the Invention

The present invention relates to a diagnosis support apparatus which supports a diagnosis concerning medical care and a diagnosis support method.

Description of the Related Art

In the field of medical care, doctors make diagnoses by observing medical images obtained by imaging apparatuses such as an OCT (Optical Coherence Tomography) and an X-ray CT apparatus. Doctors display a medical image as a target image by using a medical image display apparatus (also called a viewer), and browse the image by using various functions attached to the viewer, thereby making a diagnosis.

There has been developed a diagnosis support apparatus which supports such a diagnosis based on an image by using a computer. Japanese Patent Laid-Open No. 2014-42650 (to be referred to as patent literature 1 hereinafter) discloses a technique of estimating a lesion position based on an output from an imaging apparatus and giving an index to an estimated lesion. Japanese Patent Laid-Open No. 2009-59381 (to be referred to as patent literature 2 hereinafter) discloses a technique of obtaining, as disease condition information, inquiry results, doctor's findings, and feature amounts obtained by image processing, and extracting and presenting a diagnosis name and an image linked to the obtained disease condition information from cases stored in a database.

However, patent literature 1 is limited to presenting an index with respect to an estimated lesion. That is, since no findings concerning the estimated lesion or no cases having the estimated lesion are presented, a doctor needs to estimate a case by analogy based on the display of the lesion and the index. On the other hand, patent literature 2 only presents a diagnosis name linked to an image processing result and a typical image corresponding to the diagnosis name. This makes it difficult to comprehend the correspondence between a diagnosis target image and a case. It is therefore sometimes difficult to determine whether the presented diagnosis name is proper.

SUMMARY OF THE INVENTION

According to an embodiment of the present invention, the user can easily determine whether a similar case obtained concerning a diagnosis target medical image is proper.

According to one aspect of the present invention, there is provided a diagnosis support apparatus comprising: a detection unit configured to detect a finding and a position, on a diagnosis image as a diagnosis target medical image, which corresponds to the finding from the image; a search unit configured to search a database storing a plurality of medical images linked to findings and diagnosis names by using a finding detected by the detection unit; and a display control unit configured to simultaneously perform or switch between a first display operation of causing a display unit to display the diagnosis image, together with a finding detected by the detection unit and a position on the display which corresponds to the finding and a second display operation of causing the display unit to display a medical image found by the search unit, together with a diagnosis name associated with the medical image.

According to another aspect of the present invention, there is provided a control method for a diagnosis support apparatus, the method comprising: detecting a finding and a position on a diagnosis image as a diagnosis target medical image which corresponds to the finding from the image; searching a database storing a plurality of medical images linked to findings and diagnosis names by using the detected finding; and simultaneously performing or switching between a first display operation of causing a display unit to display the diagnosis image, together with the detected finding and a position on the display which corresponds to the finding and a second display operation of causing the display unit to display the found medical image, together with a diagnosis name associated with the medical image.

According to another aspect of the present invention, there is provided a non-transitory computer-readable storage medium storing a program for causing a computer to execute a control method for a diagnosis support apparatus, the control method comprising: detecting a finding and a position, on a diagnosis image as a diagnosis target medical image, which corresponds to the finding from the image; searching a database storing a plurality of medical images linked to findings and diagnosis names by using the detected finding; and simultaneously performing or switching between a first display operation of causing a display unit to display the diagnosis image, together with the detected finding and a position on the display which corresponds to the finding and a second display operation of causing the display unit to display the found medical image, together with a diagnosis name associated with the medical image.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3 is a flowchart showing an example of processing by the diagnosis support apparatus;

FIG. 4B is a view showing an example of second table information;

FIG. 5A is a view showing an example of the data arrangement of a database according to the first embodiment;

FIG. 5B is a view showing an example of the data arrangement of a database according to the second embodiment;

FIG. 7 is a view showing an example of display on a display unit according to the first embodiment;

FIG. 9 is a view showing an example of display on a display unit according to the second embodiment;

FIG. 11 is a view showing an example of display on a display unit according to the third embodiment.

DESCRIPTION OF THE EMBODIMENTS

Several preferred embodiments of the present invention will be described below with reference to the accompanying drawings.

First Embodiment

A diagnosis support apparatus according to the first embodiment obtains a diagnosis target medical image and information concerning the medical image, and presents image processing results on the obtained medical image (findings and the positions of the findings) as support information together with the medical image, thereby performing diagnosis support concerning the medical image. In addition, the diagnosis support apparatus searches for a case stored in a database by using an image processing result on the obtained medical image (finding), and presents, for example, the diagnosis name and medical image of the found case.

In the first embodiment, the diagnosis support apparatus processes a diagnosis target medical image (to be also referred to as a diagnosis image hereinafter), identifies a finding based on the image processing result, and presents the information on the medical image. The first embodiment will exemplify an optical coherence tomography image (to be referred to as an OCT image hereinafter) in an ophthalmic region as a diagnosis target medical image. Obviously, this is not exhaustive. Assume that in the embodiment, a diagnosis target OCT image is formed from one tomographic image (that is, a two-dimensional image) obtained by imaging in a direction passing through the optic papilla and the central fovea (macular region). An image obtained by imaging in a direction passing through the optic papilla and the central fovea will be referred to as an H scan image hereinafter. Obviously, a diagnosis target medical image is not limited to this, and the following findings and the like each are a merely example for explaining steps in processing by the diagnosis support apparatus.

Figure 1:
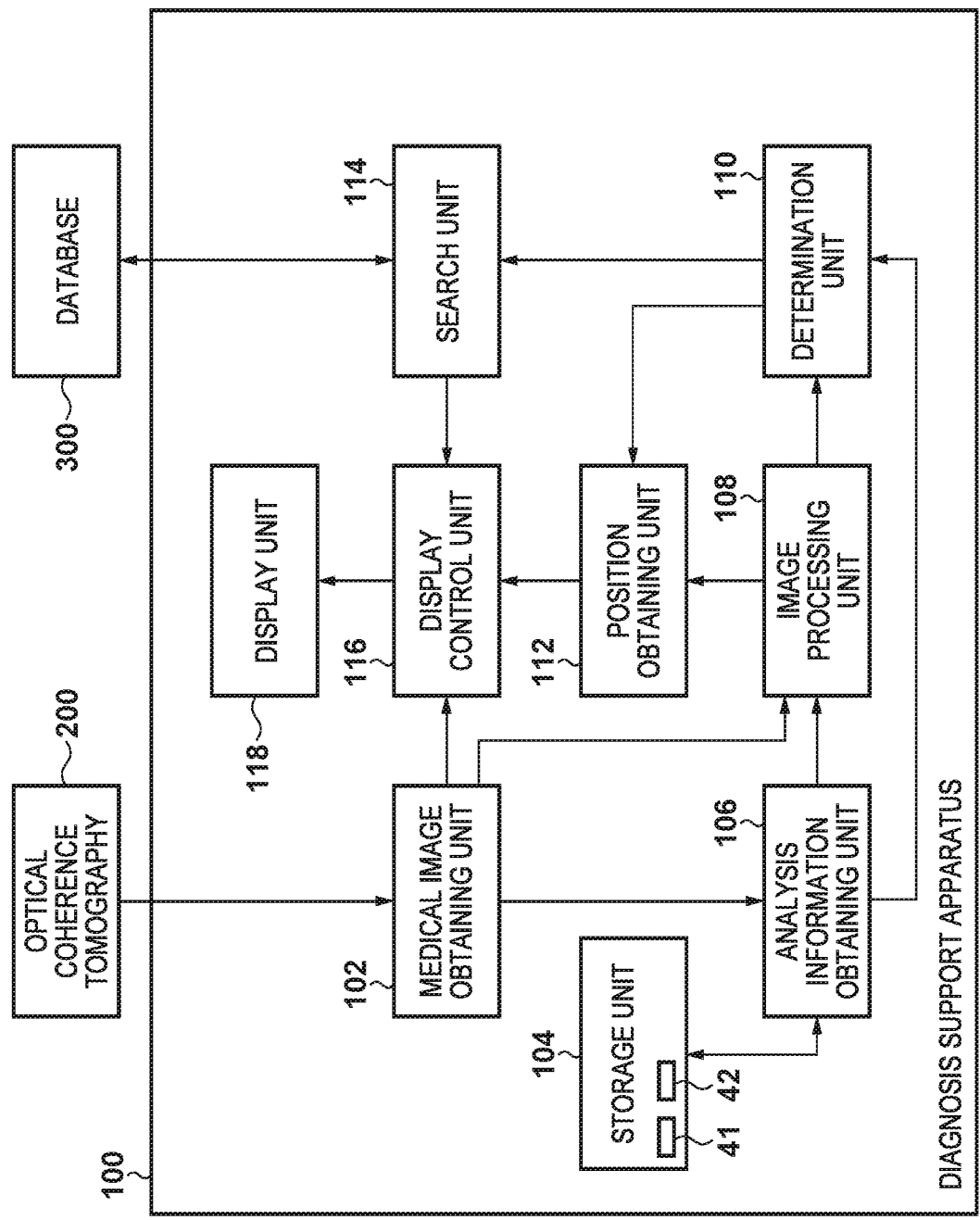
FIG. 1 is a block diagram showing an example of the functional arrangement of a diagnosis support apparatus according to the first embodiment.

FIG. 1 is a block diagram showing an example of the functional arrangement of a diagnosis support apparatus 100 according to the first embodiment. The diagnosis support apparatus 100 according to this embodiment is connected to an optical coherence tomography 200 and a database 300. The optical coherence tomography 200 irradiates the fundus with near-infrared light to obtain an OCT image (that is, a medical image) indicating a tomographic image of the retina by using coherent light obtained from the return light and reference light. The optical coherence tomography 200 then outputs the obtained medical image, information concerning the type of medical image, and information concerning the imaged region to the diagnosis support apparatus 100 via a LAN or the like. Note that the type of medical image indicates, for example, the type of medical image corresponding to a modality such as an OCT image, simple X-ray image, or CT image.

Medical images and corresponding diagnosis names and findings are linked and stored in the database 300. Specific examples of data arrangements and findings in the database 300 will be described later. In response to a request from the diagnosis support apparatus 100, the database 300 outputs a case (including a medical image, a diagnosis name, and findings) corresponding to the request to the diagnosis support apparatus 100. Note that the database 300 may be configured to be stored in a storage unit 104 (to be described later) in the diagnosis support apparatus 100.

In the diagnosis support apparatus 100, a medical image obtaining unit 102 obtains a medical image transmitted from the optical coherence tomography 200 to the diagnosis support apparatus 100, information concerning the type of medical image, and information concerning a region (imaged region) on the medical image. A medical image obtained by the medical image obtaining unit 102 is a diagnosis target medical image. Note that these pieces of information transmitted from the optical coherence tomography 200 may be stored in the storage unit 104 in advance, and may be read out from the storage unit 104 in response to a request from the user. Alternatively, an external storage device such as an FDD, HDD, CD drive, DVD drive, MO drive, or ZIP drive may be connected to the diagnosis support apparatus 100, and the medical image obtaining unit 102 may obtain the above pieces of information (the medical image, type, and region) from the external storage device. The medical image obtaining unit 102 outputs the obtained medical image to an image processing unit 108 and a display control unit 116, and outputs the information concerning the type of the obtained medical image and the corresponding region to an analysis information obtaining unit 106.

The storage unit 104 stores, for each region on a diagnosis target medical image, first table information 41 including a plurality of finding candidates to be added to each diagnosis target image and second table information 42 including parameters for image processing corresponding to the respective candidates. A parameter for image processing is that required for image processing for specifying each of a plurality of finding candidates with respect to an image as a diagnosis target. In addition, as second parameter information, a determination criterion for causing a determination unit 110 to determine whether a diagnosis target medical image includes any finding candidate is also recorded. The data arrangements of the first table information 41 and the second table information 42 will be described below with reference to FIGS. 4A and 4B.

The analysis information obtaining unit 106 obtains analysis information from the storage unit 104 based on information concerning the type and region of diagnosis target medical image obtained by the medical image obtaining unit 102. More specifically, first of all, the analysis information obtaining unit 106 obtains, from the first table information 41 in the storage unit 104, a plurality of finding candidates corresponding to the type and region of the medical image received from the medical image obtaining unit 102. The analysis information obtaining unit 106 then obtains, from the second table information 42 in the storage unit 104, a parameter for image processing corresponding to each of a plurality of finding candidates obtained by referring to the first table information 41. The analysis information obtaining unit 106 outputs the plurality of finding candidates obtained in this manner to the determination unit 110, and outputs parameters for image processing to the image processing unit 108.

The image processing unit 108 processes the medical image obtained by the medical image obtaining unit 102, based on the parameter for image processing obtained by the analysis information obtaining unit 106. The image processing unit 108 outputs this image processing result to the determination unit 110 and a position obtaining unit 112. The determination unit 110 determines whether each of a plurality of finding candidates exists (that is, corresponds to) in the medical image, based on the plurality of finding candidates obtained by the analysis information obtaining unit 106 and the image processing result obtained by the image processing unit 108. The determination unit 110 outputs this determination result to the position obtaining unit 112 and a search unit 114.

Based on the image processing result obtained by the image processing unit 108 and the finding candidate determined as corresponding to the medical image (to be referred to as the corresponding finding hereinafter) by the determination unit 110, the position obtaining unit 112 obtains information indicating the position of the medical image which corresponds to the corresponding finding. The position obtaining unit 112 outputs the information indicating the obtained position to the display control unit 116 upon linking the information to the finding candidate determined as a corresponding finding by the determination unit 110. The search unit 114 searches the database 300 by using the finding candidate determined as a corresponding finding by the determination unit 110 as a key, and obtains information concerning an image similar to the diagnosis target medical image. The obtained information concerning the image is output to the display control unit 116, together with a similarity to the medical image as a target image.

The display control unit 116 controls display based on the diagnosis target medical image obtained by the medical image obtaining unit 102, the information indicating the position on the medical image which is linked to the corresponding finding, which is obtained by the position obtaining unit 112, and the information concerning the image which is received by the search unit 114. More specifically, the display control unit 116 causes a display unit 118 to display the diagnosis target medical image, and display the corresponding finding and the information indicating the position linked to the corresponding finding. In addition, the display control unit 116 causes the display unit 118 to display the pieces of information of diagnosis names linked to similar images in descending order of similarities based on the received information concerning the similar images. The display unit 118 displays the contents of display controlled by the display control unit 116.

Note that at least some of the respective functional units of the diagnosis support apparatus 100 shown in FIG. 1 may be implemented as independent devices. Alternatively, the respective functions may be implemented by software. The respective units of this embodiment are implemented by software. An example of hardware for implementing each functional unit of the diagnosis support apparatus 100 described above by using software will be described below.

Figure 2:
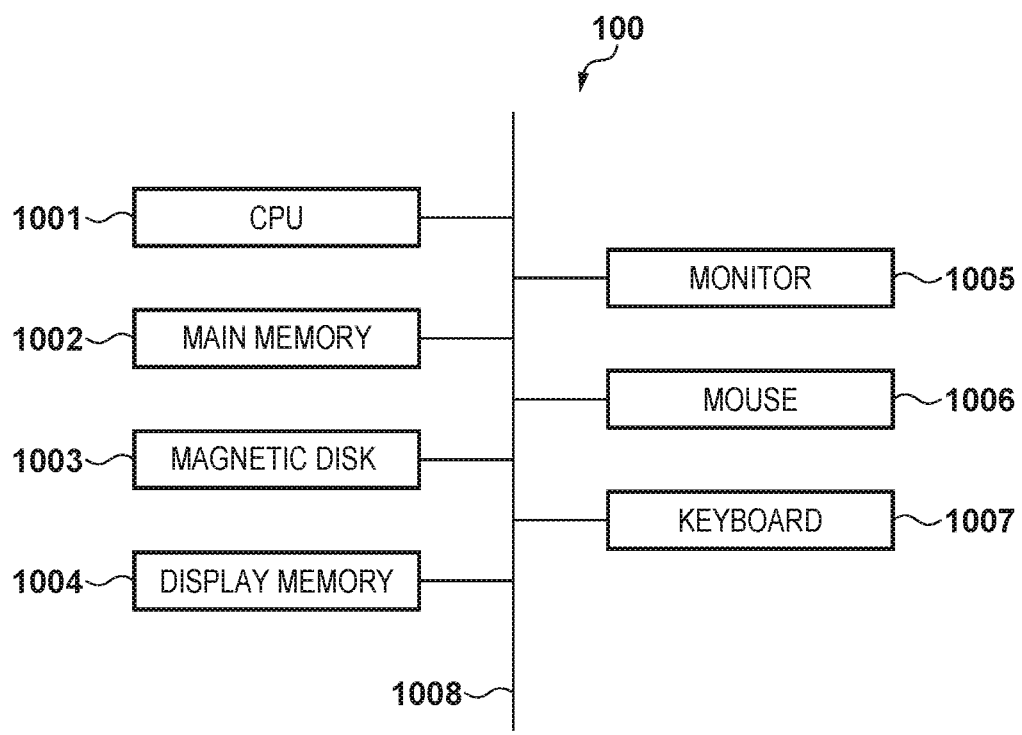
FIG. 2 is a block diagram showing an example of the hardware arrangement of the diagnosis support apparatus according to the first embodiment.

FIG. 2 is a block diagram showing an example of the hardware arrangement of the diagnosis support apparatus 100. A CPU 1001 mainly controls the operation of each constituent element. A main memory 1002 stores control programs executed by the CPU 1001, and provides a work area at the time of program execution by the CPU 1001. A magnetic disk 1003 is an example of an external storage device which stores an OS (Operating System), device drivers for peripheral devices, and programs for implementing various types of application software including programs for performing processing (to be described later). The storage unit 104 is implemented by the magnetic disk 1003. The CPU 1001 executes programs stored in the main memory 1002 and the magnetic disk 1003 to implement the functions (software) of the diagnosis support apparatus 100 shown in FIG. 1 and processing in a flowchart (to be described later).

Note that programs stored in the magnetic disk 1003 are loaded into the main memory 1002 and executed by the CPU 1001, as needed.

A display memory 1004 temporarily stores display data. A monitor 1005 is an example of the display unit 118, and is, for example, a CRT monitor or liquid crystal monitor. The monitor 1005 displays images, texts, and the like based on data from the display memory 1004. A mouse 1006 and a keyboard 1007 are operated by the user to perform a pointing input operation and input characters and the like. The respective constituent elements described above are connected to each other via a common bus 1008.

Diagnosis support processing performed by the diagnosis support apparatus 100 according to this embodiment having the above arrangement will be described next with reference to the flowchart of FIG. 3. FIG. 3 is a flowchart showing an example of diagnosis support processing performed by the diagnosis support apparatus 100. In the embodiment, the CPU 1001 executes programs for implementing the functions of the respective unit, which are stored in the main memory 1002, to function as the respective units shown in FIG. 1, thereby implementing the processing shown in FIG. 3.

In step S300, the medical image obtaining unit 102 obtains a diagnosis target medical image (diagnosis image) transmitted from the optical coherence tomography 200 and information concerning the medical image (information concerning the type of medical image and information concerning a region (imaging region) on the medical image). Assume that in this embodiment, a medical image (H scan image) obtained by imaging the fundus using the optical coherence tomography 200 is a diagnosis target. Therefore, the medical image obtaining unit 102 obtains "OCT image" as information concerning the type of medical image and "retina" as information concerning the region on the medical image. Note that in step S300, a fundus image is obtained in addition to the object OCT image. This is because the fundus image is displayed together with the OCT image in the display contents described later with reference to FIG. 7. The fundus image is obtained by, for example, a fundus camera and stored in the storage unit 104 or the like in association with the identification information of the object. The medical image obtaining unit 102 obtains the fundus image associated with the identifier of the object whose OCT image has been obtained.

Figure 4A:
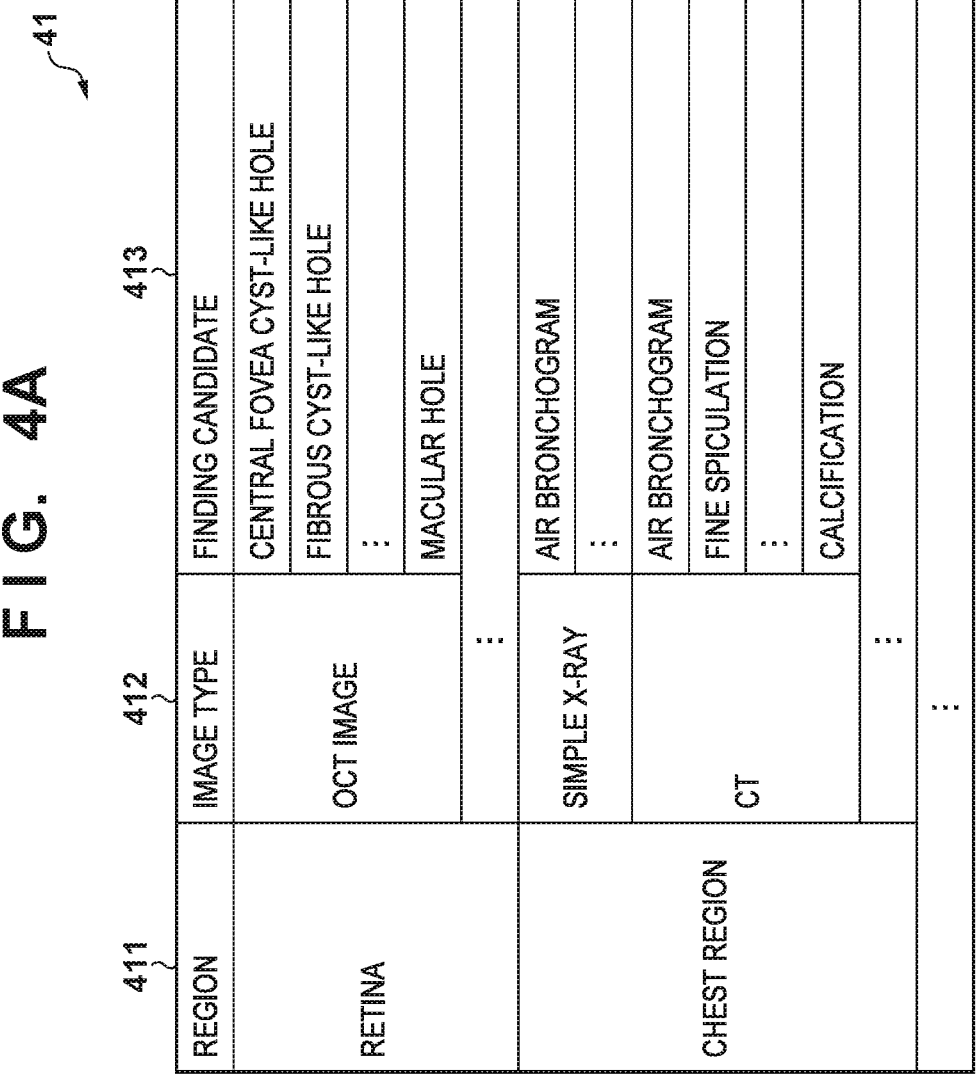
FIG. 4A is a view showing an example of first table information.

In steps S301 to S305, the diagnosis support apparatus 100 detects a finding and the position of an image corresponding to the finding from a diagnosis image which is a diagnosis target medical image. First of all, in step S301, based on the information concerning the type of diagnosis image and the information concerning the region on the diagnosis image, which are obtained in step S300, the analysis information obtaining unit 106 obtains a plurality of corresponding finding candidates from the first table information in the storage unit 104. FIG. 4A is a view showing an example of the first table information 41 stored in the storage unit 104. In the first table information 41, "image type" 412 is linked to "region" 411, and "finding candidate" 413 is linked to the information of "image type" 412. Some finding, like "air bronchogram", is linked to the information of a plurality of types of images. Obviously, some finding may be linked to a plurality of regions and a plurality of types. In this embodiment, since the region is "retina" and the type is "OCT image", finding candidates obtained include a foveal cystoid spaces, cystoid spaces in nerve layer, and macular hole.

In step S302, the analysis information obtaining unit 106 obtains, from the second table information 42 in the storage unit 104, a parameter for image processing which is required to specify each of a plurality of finding candidates obtained from the first table information 41 in step S301. Assume that this embodiment uses information concerning the type of medical image obtained in step S300 in addition to information concerning finding candidates. This is because different types of medical images require different parameters such as the pixel value of an image corresponding to each finding.

FIG. 4B is a view showing an example of the second table information 42 stored in the storage unit 104. If, for example, "finding candidate" 421 is "cystoid spaces in nerve layer" and "image type" 422 is "OCT image", "image processing parameter" 423, namely "X: 25%-75%, Z: 30%-70%, pixel value: 10 or less" is linked to them. Such an image processing parameter is obtained for each of the finding candidates obtained in step S301. Note that "determination criterion" 424 is a criterion for determining whether the image processing result obtained by the image processing unit 108 corresponds to a finding, which is used by the determination unit 110. Such determination criteria will be described in detail later in step S304.

In step S303, the image processing unit 108 processes the diagnosis target medical image obtained in step S300, based on the image processing parameter obtained in step S302. Assume that in this embodiment, the image processing unit 108 performs preprocessing for the overall diagnosis target medical image before the execution of image processing using the image processing parameter obtained in step S302. More specifically, the image processing unit 108 removes noise from the diagnosis target medical image and normalizes the image size and density values to make it ready for the application of image processing based on the parameter obtained in step S302. Assume that in the following description, an OCT image is represented by a monochrome image with 256 tones. In addition, the image processing unit 108 performs, as preprocessing, extraction of a retinal layer, more specifically, extraction of the pigmented layer of retina (RPE layer) and the internal limiting membrane (ILM). It is possible to perform such extraction by using, for example, a known contour line extraction algorithm such as Snakes.

The image processing unit 108 then performs image processing based on image processing parameters respectively corresponding to a plurality of finding candidates. The following description will describe an example of using the parameter "X: 25%-75%, Z: 30%-70%, pixel value: 10 or less" for image processing for "cystoid spaces in nerve layer". In this instance, in accordance with the above parameter for the image normalized by preprocessing, the image processing unit 108 extracts pixels having pixel values of 10 or less from a rectangular range defined by an X-coordinate of 25% to 75% and a Z-coordinate of 30% to 70% of the OCT image. The image processing unit 108 performs such processing for each of a plurality of finding candidates (obviously, the contents of image processing vary for the respective finding candidates in accordance with parameters).

In step S304, the determination unit 110 determines, based on the result of image processing executed in step S303, whether each of the plurality of finding candidates obtained in step S302 corresponds to the diagnosis target medical image (exists on the diagnosis target medical image). For example, with regard to the finding candidate "cystoid spaces in nerve layer", the determination unit 110 calculates the aspect ratio (short side/long side) of each region including adjacent pixels of pixels extracted according to an image processing parameter. The determination unit 110 then determines a region having an aspect ratio of, for example, 0.7 or less as a region corresponding to "cystoid spaces in nerve layer". Alternatively, with regard to the finding candidate "posterior vitreous detachment", the determination unit 110 determines a line extracted by thinning processing as a line corresponding to the finding candidate when the length of the extracted line is equal to or more than a threshold (for example, 20% of the length of the image in the X direction). Note that these determination criteria are obtained by referring to "determination criterion" 424 stored for each finding candidate in the second table information 42 stored in the storage unit 104. Note that the method of holding determination criterion is not limited to this. It is possible to use third table information (not shown) in which determination criteria are linked to finding candidates and image types.

Figure 6:
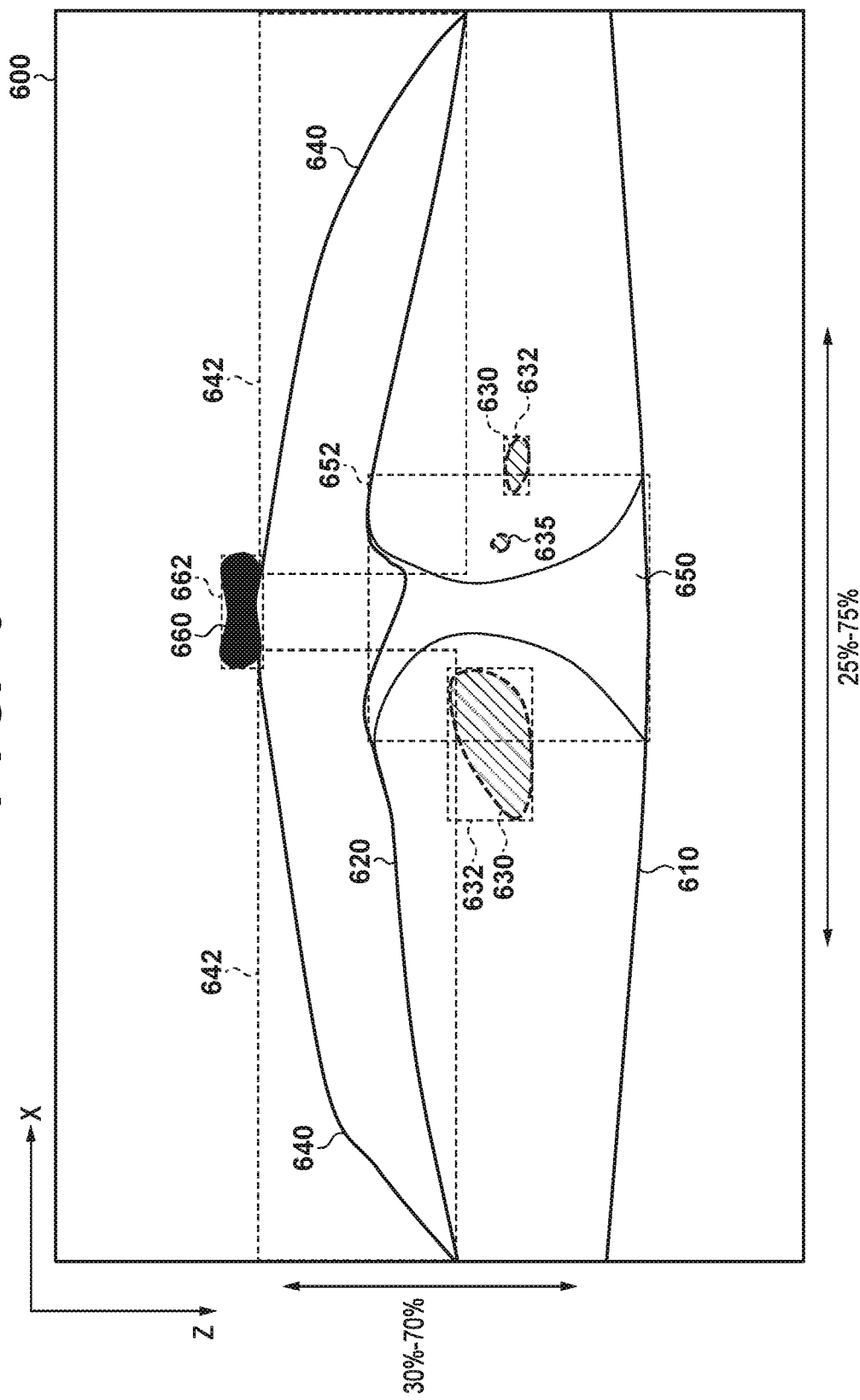
FIG. 6 is a view showing an example of performing image processing and specifying the position of each finding.

FIG. 6 is a view showing the execution results of image processing in step S303 and the determination results in step S304. An RPE layer 610 and an ILM 620 shown in FIG. 6 are results (preprocessing results) obtained by performing noise removal and normalization with respect to an OCT image 600 and then performing extraction using a known extraction technique. Note that in this instance, the existence of a macular hole 650 makes it impossible to properly perform extraction at an image central portion (central fovea) of the ILM 620.

A corresponding region 630 of the cystoid spaces in nerve layer and a non-corresponding region 635 of the cystoid spaces in nerve layer indicate regions extracted by a parameter for image processing for the finding candidate "cystoid spaces in nerve layer" in step S303. As shown in FIG. 6, the corresponding region 630 of the cystoid spaces in nerve layer has an aspect ratio of 0.7 or less (that is, horizontally long), and hence is determined as a region corresponding to "cystoid spaces in nerve layer". In contrast to this, the non-corresponding region 635 of the cystoid spaces in nerve layer has an aspect ratio exceeding 0.7, and hence is determined as a region which does not correspond to the "cystoid spaces in nerve layer". Likewise, a corresponding portion 640 of the posterior vitreous detachment indicates a line extracted by a parameter for image processing corresponding to the finding candidate "posterior vitreous detachment" in step S303. In this instance, the length of the extracted line in the X direction exceeds 20% of the length of an image in the X direction, which is a threshold, and hence is determined as a portion corresponding to "posterior vitreous detachment". In step S304, the determination unit 110 performs such determination with respect to each of a plurality of finding candidates. In the example shown in FIG. 6, the macular hole 650 and a operculum 660 are determined as corresponding to finding candidates, in addition to the above findings.

In step S305, based on the results of the image processing executed in step S303 and the finding candidates determined in step S304 as corresponding findings, the position obtaining unit 112 obtains information indicating the positions of portions on the medical image which correspond to the findings. Although any information which can specify a position can be used as the information indicating the positions, this embodiment generates and obtains information concerning a rectangle (for example, the coordinates of four vertexes) circumscribing an image region determined by the determination unit 110 as corresponding to a finding candidate.

In the example shown in FIG. 6, the position of a rectangle 632 circumscribing the corresponding region 630 determined as "cystoid spaces in nerve layer" in step S304 is obtained as the position information of the cystoid spaces in nerve layer. In addition, the position of a rectangle 642 circumscribing the corresponding region 640 determined as "posterior vitreous detachment" is obtained as the position information of the posterior vitreous detachment. Such information indicating a position is obtained with respect to each of a plurality of finding candidates determined in the above manner. In the example shown in FIG. 6, the positions of a rectangle 652 circumscribing the macular hole 650 and a rectangle 662 circumscribing the operculum 660 are obtained. Note that pieces of information indicating the position of the same finding may be obtained concerning the respective regions. Alternatively, priority levels may be assigned to the respective regions, and information indicating the position of a region with the highest priority level may be obtained as information indicating the position of the finding. A priority level can be determined based on, for example, the magnitude of the area of a rectangle, the distance from the center of the image, or the distance from an end of the image.

In step S306, the search unit 114 obtains similar cases from the database 300 storing a plurality of cases by using the findings determined as the corresponding findings as keys in step S304. FIG. 5A shows an example of the data arrangement of the database 300 according to this embodiment. Each case stored in the database 300 includes the ID (identification number) of the case, imaging date, diagnosis name, findings, image type, and medical images (OCT image and fundus image). Note that each case stored in the database 300 is obtained by making the doctor specify a finding, position, and diagnosis name corresponding to a medical image in advance. Such cases may use literature information such as textbook information. Alternatively, the doctor may specify findings and diagnosis names with respect to cases acquired for the database.

In addition, the search unit 114 may obtain, from the database 300 as a similar case, only a case which a search key perfectly matches or obtain a case which the search key partially matches. Alternatively, the search unit 114 may calculate similarities by some method and obtain a predetermined number of images in descending order of similarities. Assume that in this embodiment, the search unit 114 obtains similar cases which search keys (findings) perfectly match. A method using the similarities of findings will be described in a modification.

In step S307, the display control unit 116 performs the first display operation of making the display unit 118 display a diagnosis target medical image (an OCT image 710 in FIG. 7) and the second display operation of making the display unit 118 display a medical image (an OCT image 730 in FIG. 7) of a similar case found from the database 300. Note that in the first display operation, the diagnosis image obtained in step S300 is displayed together with the findings and the positions on the image which correspond to the findings, which are detected in steps S301 to S305. In the second display operation, the similar case found in step S306 (for example, a medical image and a diagnosis name associated with the medical image) is displayed. In addition, the display unit 118 may simultaneously perform the first display operation and the second display operation or may switch (alternatively) and perform the display operations in accordance with a user operation. The following description will describe an example of simultaneously performing the first display operation and the second display operation. In addition, in the second display operation, it is preferable to display a found medical image together with findings associated with the medical image and information indicating the positions of the findings. This is because the user can more easily comprehend the correspondence between the diagnosis image and findings on a medical image of a similar case.

More specifically, the display control unit 116 uses the information indicating the positions of the findings obtained in step S305 to superimpose/display the information concerning the findings determined as the corresponding findings on the diagnosis target medical image obtained in step S300. Assume that in this embodiment, the superimposition/display position of each finding determined as a corresponding finding is decided according to the following display rules: (1) not to superimpose/display any finding on information indicating the position of another finding determined as a corresponding finding; (2) to display the character information of a finding on the lower side of the RPE layer in the Z direction or on the upper side of the ILM in the Z direction; and (3) to add a marker (for example, an arrow) near each information indicating the position of a finding determined as a corresponding finding when information indicating the position of the finding exists between the RPE layer and the ILM in the Z direction. Obviously, the above display rules are examples, and are not exhaustive.

Figure 7:
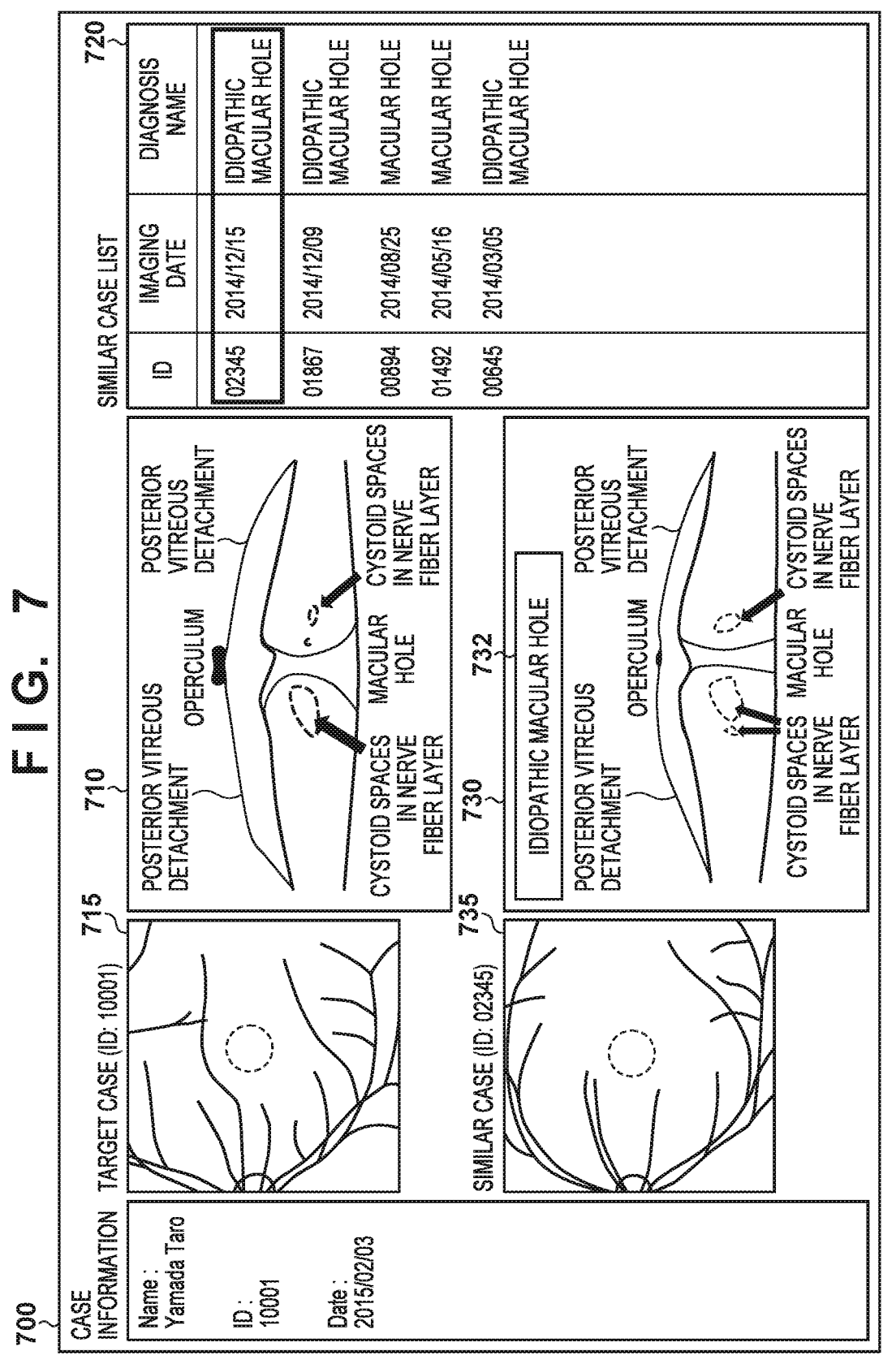

The display control unit 116 further displays a medical image included in a similar case, of the similar cases obtained in step S306, which has the highest similarity and information concerning a diagnosis name linked to the medical image (an OCT image 730 and a diagnosis name 732 in FIG. 7). Assume that in this embodiment, since a case which a search key perfectly matches is obtained as a similar case in step S306, a medical image whose imaging date closer to the imaging date of the diagnosis target medical image obtained in step S300 exhibits a higher similarity. Therefore, a medical image of a case, of found similar cases, whose imaging date is closest to that of the diagnosis target medical image is displayed. In this embodiment, the similar cases found in step S306 are managed in the form of a list. In addition, a similar case list 720 in FIG. 7 is displayed, and one similar case in the list is displayed on a side of the diagnosis target medical image obtained in step S300.

Note that the diagnosis support apparatus 100 may automatically select a similar case to be displayed as the OCT image 730 or may accept the selection by a user input operation. When automatically selecting similar cases as display targets, the diagnosis support apparatus 100 may select similar cases from found similar cases in descending order of similarities. When accepting selection by a user input operation, for example, the use of a user interface which makes the user select one case from the displayed list of similar cases found in step S306 (the similar case list 720) can implement the selection of a case as a display target.

Assume that in this embodiment, a similar case with the latest imaging date is a case to be displayed first, and similar cases to be subsequently displayed are decided as display targets from a similar case list like that described above in accordance with user selections. Note that a method of displaying similar cases is not limited to this. For example, medical images of a plurality of similar cases and pieces of information concerning diagnosis names linked to them may be displayed in a form that allows comparison with the diagnosis target medical image obtained in step S300 or in a form that allows comparison with all images.

FIG. 7 is a view showing an example of display contents displayed on the display unit 118 by the display control unit 116. Display contents 700 displayed on the display unit 118 by the display control unit 116 include an OCT image 710 (first display) with findings and information indicating their positions being superimposed/displayed on a diagnosis image and a fundus image 715 corresponding to the diagnosis image. The display contents 700 also include a similar case list 720 (a list displaying similar medical images in descending order of similarities). In addition, the display contents 700 include information indicating one similar case (in this instance, a similar case with the latest imaging date) in the similar case list 720. The information indicating this similar case includes the OCT image 730 with findings being superimposed/displayed on a medical image associated with the selected case, the diagnosis name 732, and a fundus image 735 corresponding to the medical image.

On the OCT images 710 and 730, pieces of information concerning findings determined as existing in the OCT images are superimposed/displayed based on pieces of information indicating the positions of the findings according to the above display rules. For example, with regard to "cystoid spaces in nerve layer", since information indicating the position of the finding is located between the RPE layer and the ILM in the Z direction, the character information of the finding is displayed on the lower side of the RPE layer in the Z direction. In addition, a marker (an arrow in the example in FIG. 7) is added near the information indicating the position of the finding. In addition, with regard to "posterior vitreous detachment", since information indicating the position of the finding is located on the upper side of the ILM in the Z direction, the character information of the finding is displayed near the information indicating the position of the finding so as not to overlap the ILM. Likewise, with regard to "macular hole" and "operculum", pieces of character information of the findings are displayed near the findings.

Note that as described above, when the user selects another similar case as a display target from the similar case list 720, the display control unit 116 displays a medical image associated with the selected similar case on the display unit 118. More specifically, the display control unit 116 displays, on the display unit 118, the medical image of the similar case selected from the similar case list 720, the diagnosis name, and the findings as the OCT image 730 and the diagnosis name 732, and also displays the fundus image of the selected similar case as the fundus image 735.

Note that the user performs selection with a pointing device such as a mouse via a GUI. If the display unit 118 is formed from a touch panel, the user may perform selection by operating a list displayed on the touch panel as the display unit 118. For example, the user can select a case on the list by double-clicking the case. Alternatively, the user may temporarily select a case on the list by a tapping operation and actually select the temporarily selected case by performing a flicking operation or swiping operation in the horizontal direction. Alternatively, the user may sequentially select cases located below the temporarily selected case on the list by continuously performing a flicking operation or swiping operation while the case is temporarily selected.

According to the first embodiment described above, the diagnosis support apparatus 100 obtains a corresponding finding candidate and a parameter for image processing for the derivation of the finding candidate based on the information of a region on a diagnosis target medical image. The diagnosis support apparatus 100 then determines the corresponding finding and specifies the position of the finding by processing the diagnosis target medical image based on the obtained image processing parameter, and superimposes/displays the result on the diagnosis target medical image.

The diagnosis support apparatus 100 searches for a similar case by using the corresponding finding as a key, and displays a medical image associated with the found similar case together with findings and a diagnosis name. This processing allows the doctor to check, on the diagnosis target medical image, the finding determined as a corresponding finding, its position, the medical image of the similar case, a diagnosis name, and findings. In this manner, the doctor can browse the diagnosis name of the case similar to the state of the diagnosis target medical image, together with the corresponding medical image. This can reduce the load associated with the diagnosis.

Note that in the above embodiment, the first table information 41 has both the type of medical image and a region linked to a finding candidate. However, this is not exhaustive. For example, when the diagnosis support apparatus 100 is dedicated to ophthalmic medical images, no information is required concerning regions. When the diagnosis support apparatus 100 is dedicated to OCT images, there is no need to link to the type of medical image. As in the above embodiment, however, letting the first table information 41 have information linking "region of object included in medical image" and "type of medical image" to "finding candidate" will improve the versatility of the diagnosis support apparatus 100 in terms of regions on images and image types.

(Modification 1-1)

In the first embodiment, in step S306, the search unit 114 uses the finding determined as a corresponding finding in step S304 as a key and obtains only a case which the search key perfectly matches. However, this is not exhaustive. For example, the search unit 114 may obtain a medical image which the search key partially matches or may obtain a medical image by calculating the similarity of the search key.

As the similarity of a search key (finding), for example, the cosine similarity obtained by calculating the similarities of vectors can be used. This operation will be described in detail below. First of all, the determination unit 110 generates a finding vector by using the plurality of finding candidates obtained in step S301 and the finding determined as a corresponding finding in step S304. A finding vector can be generated by regarding each finding candidate as a vector element, with 1 being assigned to each finding determined as a corresponding finding (existing) in a diagnosis target medical image, and 0 being assigned to each finding determined as not a corresponding finding. For example, when there are 20 finding candidates, a 20-dimensional finding vector is generated.

The determination unit 110 then generates the finding vector of a similar case stored in the database 300, and calculates the similarity between it and a finding vector generated with respect to the diagnosis target medical image. Note that a finding vector may be stored in advance for each case in the database 300. Letting Vt be the finding vector of the diagnosis target medical image and Vs be the finding vector of a medical image stored in the database 300, a cosine similarity is represented by $$\cos(\vec{V}_t, \vec{V}_s) = \frac{\vec{V}_t \cdot \vec{V}_s}{|\vec{V}_t||\vec{V}_s|} \quad (1)$$

As this cosine similarity becomes closer to 1, it indicates that the two vectors are similar. As the cosine similarity becomes closer to 0, it indicates that the two vectors are not similar. When using such similarities, a predetermined number of cases are preferably displayed on the similar case list 720 in descending order of similarities in step S307. Note that this modification can also be applied to other embodiments.

(Modification 1-2)

In the first embodiment, the doctor specifies a finding of a case stored in the database 300 and the position of the finding. However, they may be specified by another method. For example, the processing in steps S301 to S305 may be performed for a case (medical image) stored in the database 300 to link a corresponding finding to the position information of the finding. Alternatively, after the processing in step S307, a corresponding case (a diagnosis target medical image, findings, and a diagnosis name) may be additionally stored in the database.

(Modification 1-3)

In the first embodiment, the search unit 114 searches cases stored in the database 300 for a similar case. However, it is always necessary to search for a similar case from the database 300 connected to the outside. For example, case information equivalent to the information in the database 300 may be stored in the storage unit 104 in advance, and the search unit 114 may search the case information stored in the storage unit 104 for a similar case. In addition, for case information stored in the storage unit 104, partial databases extracted in accordance with various conditions such as an installation place and time may be used. That is, pieces of case information which can be presented as similar cases may be switched between them in accordance with conditions such as an installation place and a user. Furthermore, the first table information and the second table information stored in the storage unit 104 may be switched between them in accordance with conditions such as a user, installation place, and time. For example, when using CT images or the like, the first table information 41 and the second table information 42 may be switched between them in accordance with a resolution and a slice thickness. At the same time, partial databases may be switched between them. In this instance, case information may be an image having the same resolution and slice thickness as those of a CT image as input information. For example, if the installation place of the apparatus indicates the discrimination between clinical departments such as an ophthalmic department and an internal medicine department, partial databases extracted from the database 300, the first table information 41, and the second table information 42 may be switched between them in accordance with the clinical department.

Second Embodiment

Figure 8A:
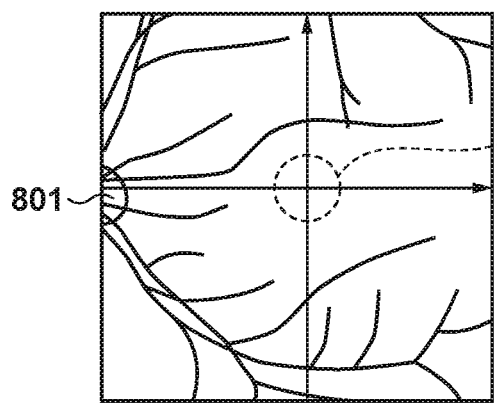
FIGS. 8A and 8B are views each showing an example of an imaging method for an optical coherence tomography.
Figure 8B:
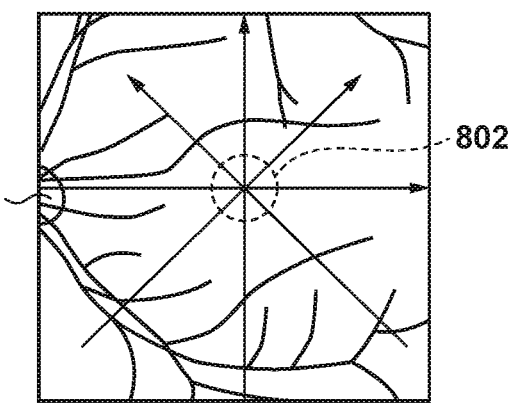

The first embodiment is configured to present support information by using one OCT image as a diagnosis target medical image. When performing examinations by using an optical coherence tomography 200, OCT images are sometimes obtained from a plurality of directions for one examination. For example, as shown in FIG. 8A, two tomographic images are sometimes obtained, including a tomographic image obtained by an H scan passing through an optic papilla 801 and a central fovea 802 (to be referred to as an H scan image hereinafter) and a tomographic image obtained by a V scan passing through the central fovea 802 and intersecting the H scan tomographic image at a right angle (to be referred to as a V scan image). Alternatively, as shown in FIG. 8B, a plurality of tomographic images are sometimes obtained by scans at predetermined angular intervals, passing through the central fovea 802.

A diagnosis support apparatus according to the second embodiment obtains a plurality of medical images obtained by imaging from a plurality of directions, and presents support information on a medical image by using image processing results on the obtained medical images, thereby performing diagnosis support concerning the medical image. This embodiment will describe an example of obtaining two tomographic images (H scan image and V scan image) like those shown in FIG. 8A from one object (fundus). The functional arrangement of the diagnosis support apparatus according to the second embodiment is the same as that of the first embodiment (FIG. 1). In addition, the hardware arrangement of a diagnosis support apparatus 100 is the same as that in the first embodiment (FIG. 2). Diagnosis support processing performed by the diagnosis support apparatus 100 according to the second embodiment will be described with reference to the flowchart of FIG. 3. Although diagnosis support processing according to the second embodiment is almost the same as that in the first embodiment, they partly differ from each other. Diagnosis support processing performed by the diagnosis support apparatus 100 according to the second embodiment will be described below.

In step S300, a medical image obtaining unit 102 obtains a plurality of medical images (a set of diagnosis target medical images) obtained by imaging from a plurality of directions, which are transmitted from the optical coherence tomography 200, and information concerning the types of obtained medical images and information concerning regions on the medical images. Note that one piece of information concerning the type of obtained medical image and one piece of information concerning a region on a medical image may be obtained for each medical image set. Alternatively, such pieces of information may be obtained for each medical image included in a medical image set. Assume that in the following description, one piece of information concerning the type of medical image and one piece of information concerning a region on a medical image are obtained for one medical image set.

As in the first embodiment, in step S301, an analysis information obtaining unit 106 refers to first table information 41 stored in a storage unit 104 to obtain a plurality of finding candidates corresponding to pieces of information concerning the type of medical image and a region, which are obtained in step S300. In addition, processing in steps S302 to S305 is the same as that in the first embodiment except that the processing is performed for each of a plurality of medical images included in a diagnosis target medical image set.

In step S306, a search unit 114 obtains a similar image from a database 300 by using the finding determined as a corresponding finding in step S304 as a key. As shown in FIG. 5B, an identifier, an imaging date, a diagnosis name, two OCT images (H scan image and V scan image), and a fundus image are associated with each other and recorded as a case in the database 300. In this manner, the database 300 stores, as one case, a medical image set including a plurality of medical images of one object region obtained in a plurality of directions, while linking them to findings and a diagnosis name. In steps S301 to S305, findings concerning the plurality of diagnosis images of one object region obtained in a plurality of directions and positions on the images which correspond to the findings are obtained. In step S306, the search unit 114 searches the database 300 for a similar case based on the detected findings.

In this embodiment, the search unit 114 searches the database 300 by using, as a key, a finding determined as a corresponding finding in one medical image (that is, a medical image obtained by imaging from a given direction) of a plurality of medical images included in a diagnosis target medical image set. In this instance, the search unit 114 performs a search by comparing a finding detected from a diagnosis image, of a plurality of diagnosis images, which is obtained in a given direction with a finding associated with a medical image, of a plurality of medical images included in a case stored in the database 300, which is obtained in a given direction. For example, a medical image obtained in the same direction as that in which a medical image as a search source is obtained in the database 300 is a search target. In this embodiment, since a search for a similar case is made by using a finding determined as a corresponding finding concerning an H scan image as a diagnosis target, and hence a finding on the H scan image is used as a key for a search for an H scan image in the database 300.

In addition, as in the first embodiment, assume that the search unit 114 searches for a medical image which a search key perfectly matches. Note that when there are a plurality of medical images obtained by imaging from different directions in a found case, they are collectively obtained as a medical image set in one similar case. As described above, in this embodiment, the search unit 114 searches the database 300 by using, as keys, a finding and a direction existing in one of a plurality of medical images included in a diagnosis target medical image set. The search unit 114 then obtains a case (medical image set) including the found medical image as one of the medical images in the plurality of directions from the database 300.

In step S307, a display control unit 116 causes a display unit 118 to perform the first display operation of displaying at least one of a plurality of diagnosis images and the second display operation of displaying at least one of a plurality of medical images included in a similar case found by the search unit 114. The display unit 118 may simultaneously perform the first display operation and the second display operation or may switch (alternatively) and perform the display operations in accordance with a user operation. Assume that in this embodiment, the display unit 118 simultaneously performs the first display operation and the second display operation.

More specifically, the display control unit 116 causes the display unit 118 to display at least one of a plurality of medical images included in a diagnosis target medical image set in the same form as that in the first embodiment. In addition, the display control unit 116 causes the display unit 118 to display a medical image included in a found similar case and the information of a diagnosis name linked to it in the same manner as in the first embodiment. In the second embodiment, however, since a case including a medical image set is found, at least one of the plurality of medical images included in the medical image set of the case is displayed. When displaying the found medical image first, the display control unit 116 selects a medical image, of a diagnosis target medical image set, which is obtained in the same direction as a medical image as a display target from a similar case with the highest similarity, and causes the display unit 118 to display the selected image.

In addition, in this embodiment, as in the first embodiment, similar cases (medical image sets of cases and the information of diagnosis names linked to them) are managed in a list, and a similar case list 920 (FIG. 9) is displayed. One case in the similar case list 920 is displayed in the form that allows comparison with a diagnosis target medical image set obtained in step S300. If, for example, an image set of a similar case includes a plurality of medical images obtained by imaging from different directions, at least one of the medical images is displayed in the form that allows comparison. When displaying medical images in accordance with the selection of cases from a similar case list, the display unit displays first a medical image, of the medical images included in the diagnosis target medical image set obtained in step S300, which is obtained in the same direction as that of the medical image displayed in step S307. Note that a medical image obtained from a different direction may be displayed.

The second embodiment will exemplify an arrangement configured to select and display a diagnosis target medical image set obtained in step S300 and one medical image from each medical image of the medical image set found as a similar case. Note however that the diagnosis support apparatus 100 may automatically select a display target medical image from a diagnosis target medical image set and a similar case or the user may select such an image. For example, the user can perform selection by a user input operation using a user interface such as a button. A method of implementing such a user interface according to this embodiment will be described later with reference to FIG. 9.

Figure 9:
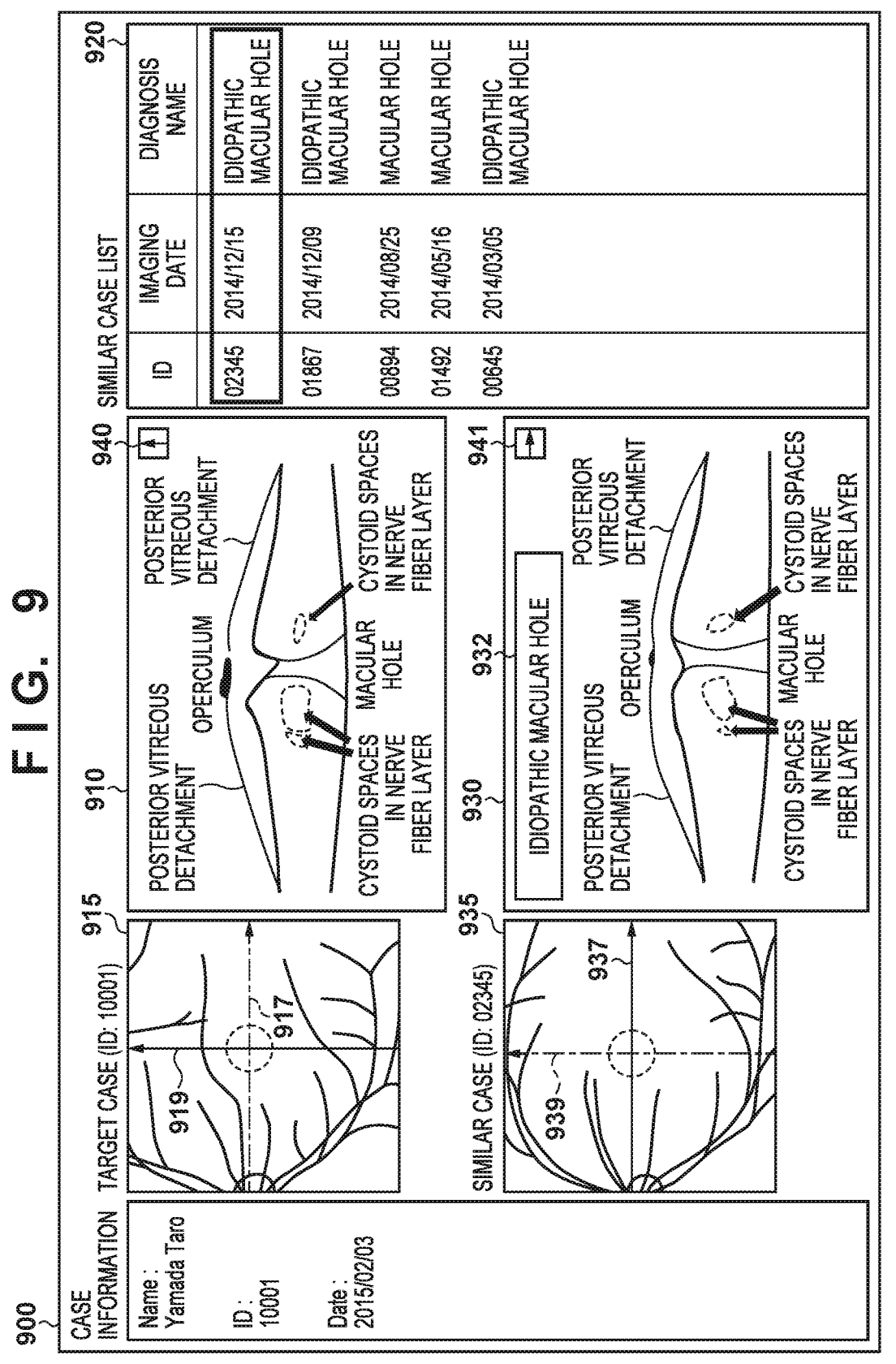

FIG. 9 is a view showing an example of display contents displayed by the display unit 118 according to the second embodiment. Display contents 900 displayed by the display unit 118 include an OCT image 910 as a medical image selected from the medical image set of a similar case and a fundus image 915 corresponding to the OCT image 910. An arrow indicating the direction in which the OCT image is obtained is superimposed/displayed on the fundus image 915. A horizontal arrow 917 on the fundus image 915 corresponds to the direction of an H scan image, and a vertical arrow 919 corresponds to the direction of the V scan image. In addition, the display contents 900 include the similar case list 920. Note that a fundus image is obtained by performing imaging such that the optic papilla and central fovea (macular region) are arranged side by side in the horizontal direction, as shown in FIG. 9. Note however that the optic papilla and the central fovea hole (macular hole) may be extracted from a fundus image by a known method, and a direction connecting them to each other may be set as an H direction.

The display contents 900 further include an OCT image 930, like a diagnosis target medical image, which is a medical image selected from the medical image set of one similar case designated from the similar case list 920. In addition, findings and a diagnosis name 932 which are associated with the OCT image 930 are superimposed/displayed on the OCT image 930. The display contents 900 further include a fundus image 935 corresponding to the OCT image 930. The fundus image 935 has a horizontal arrow 937 and a vertical arrow 939. Note that a description of the superimposition/display of findings associated with the OCT images 910 and 930 and selection by the user with respect to the similar case list 920 is the same as that in the first embodiment, and hence will be omitted.

In the second embodiment, when the user selects a similar case from the similar case list 920, one of the plurality of medical images included in the selected similar case is displayed as the OCT image 930. In addition, the arrows displayed on the fundus images 915 and 935 are used as a user interface for selecting medical images to be displayed as the OCT images 910 and 930 from a diagnosis target medical image set and the plurality of medical images of a selected similar case.

More specifically, the user performs selection by clicking either the horizontal arrow 917 or the vertical arrow 919, superimposed/displayed on the fundus image 915, with, for example, the mouse. The display control unit 116 then selects a medical image obtained by imaging in the direction corresponding to the arrow selected by the user from a diagnosis target medical image set, and displays the selected image as the OCT image 910. Likewise, in accordance with the selection of either the horizontal arrow 937 or the vertical arrow 939 superimposed/displayed on the fundus image 935, the display control unit 116 selects a medical image in a direction corresponding to the selected arrow from the selected similar case, and displays the selected image as the OCT image 930.

In addition, on the fundus images 915 and 935, currently selected arrows are preferably displayed so as to be discriminated from the remaining arrows. In the example shown in FIG. 9, the arrows displayed in solid lines indicate selected arrows. That is, the vertical arrow 919 is selected on the diagnosis target medical image, and the OCT image 910 (V scan image) in a direction corresponding to the vertical arrow 919 is displayed. On the other hand, the horizontal arrow 937 is selected on the similar case selected from the similar case list 920, and the OCT image 930 (H scan image) in a direction corresponding to the horizontal arrow 937 is displayed. In addition, icons 940 and 941 indicating the imaging directions of the respective medical images are displayed on the OCT image 910 and the OCT image 930, respectively. Note that in an initial state (that is, before the direction of each medical image to be displayed is selected by a user input operation), a medical image in the imaging direction of a medical image from which a finding used for a search in step S306 is detected is displayed.

As described above, according to the second embodiment, when medical images include a plurality of images obtained by imaging from a plurality of directions, it is possible to check not only an image obtained from a search target direction but also images obtained from other directions with a simple operation. That is, since the doctor can easily switch and check various images, the load of making a diagnosis can be reduced.

(Modification 2-1)

In the second embodiment, in step S306, the search unit 114 uses one of a plurality of diagnosis images as a search source, and searches the database 300 by using a finding candidate determined as corresponding to the search source as a key. At this time, a medical image obtained by imaging from the same direction as that of the search source is a search target. That is, in the second embodiment, the direction of a medical image from which a finding as a search key is detected matches the direction of a medical image as a search target in the database 300. However, the manner of selecting a finding as a search key from findings detected from a diagnosis target medical image set and the manner of selecting a medical image as a search target in the database 300 are not limited those in the above embodiment.

For example, it is possible to generate search keys concerning medical images, of a plurality of medical images included in a diagnosis target medical image set, which are obtained in two or more directions or all the directions, and to obtain a medical image set including similar medical images in the directions. Consider, for example, a situation in which a plurality of medical images included in a diagnosis target medical image set as a search source are an H scan image and a V scan image. In this instance, findings respectively detected from the H scan image and the V scan image become search keys. It is also possible to obtain, as a similar case, a case having an H scan image similar to an H scan image of a search source among images existing in the database 300 and also having a V scan image similar to a V scan image of the search source.

In addition, in the second embodiment, a medical image obtained from the same direction as that in which a medical image as a search source is obtained is set as a search target. However, a medical image obtained from another direction may be included as a search target. That is, a search may be performed by comparing a finding detected from a diagnosis image, of a plurality of diagnosis images, which is obtained in one direction with a finding associated with a medical image in each direction in the database. If, for example, a search source image is an H scan image, a V scan image existing in the database 300 may be set as a search target image. Alternatively, if a search source image is an H scan image, an H scan image and a V scan image existing in the database 300 may be set as search target images.

In addition, in the second embodiment, the search unit 114 uses a finding determined as a corresponding finding on one medical image as a key for a search. However, this is not exhaustive. For example, findings determined as corresponding findings on two or more medical images or all the medical images of a plurality of medical images included in a diagnosis target medical image set may be ANDed or ORed, and the result may be used as a search key. In this instance, with respect to the respective cases in the database 300 as a search target, findings linked to a plurality of medical images may be ANDed or ORed.

Third Embodiment

In the first and second embodiments, a search for a similar case is performed by using information indicating the presence/absence of a finding. The third embodiment will describe an example of using clinical information and a quantitative determination result on a finding in addition to the above information. A diagnosis support apparatus according to the third embodiment obtains a diagnosis target medical image, information concerning the medical image (the type of medical image and a region on it), and clinical information. The apparatus then presents support information on the medical image by using an obtained image processing result on the medical image, and also presents a similar case obtained in consideration of the clinical information, the finding, and a quantitative determination result, thereby performing diagnosis support associated with the medical image.

The third embodiment will describe an example of performing image processing for a chest X-ray CT image, identifying an finding based on the image processing result, and presenting the resultant information on a medical image. Assume that a diagnosis target medical image is a chest X-ray CT image and a three-dimensional medical image formed from a plurality of tomographic images in the craniocaudal direction (so-called axial tomographic images). Obviously, however, target images are not limited to them, and findings and the like described below each are a merely example for explaining steps in processing by the diagnosis support apparatus.

Figure 10:
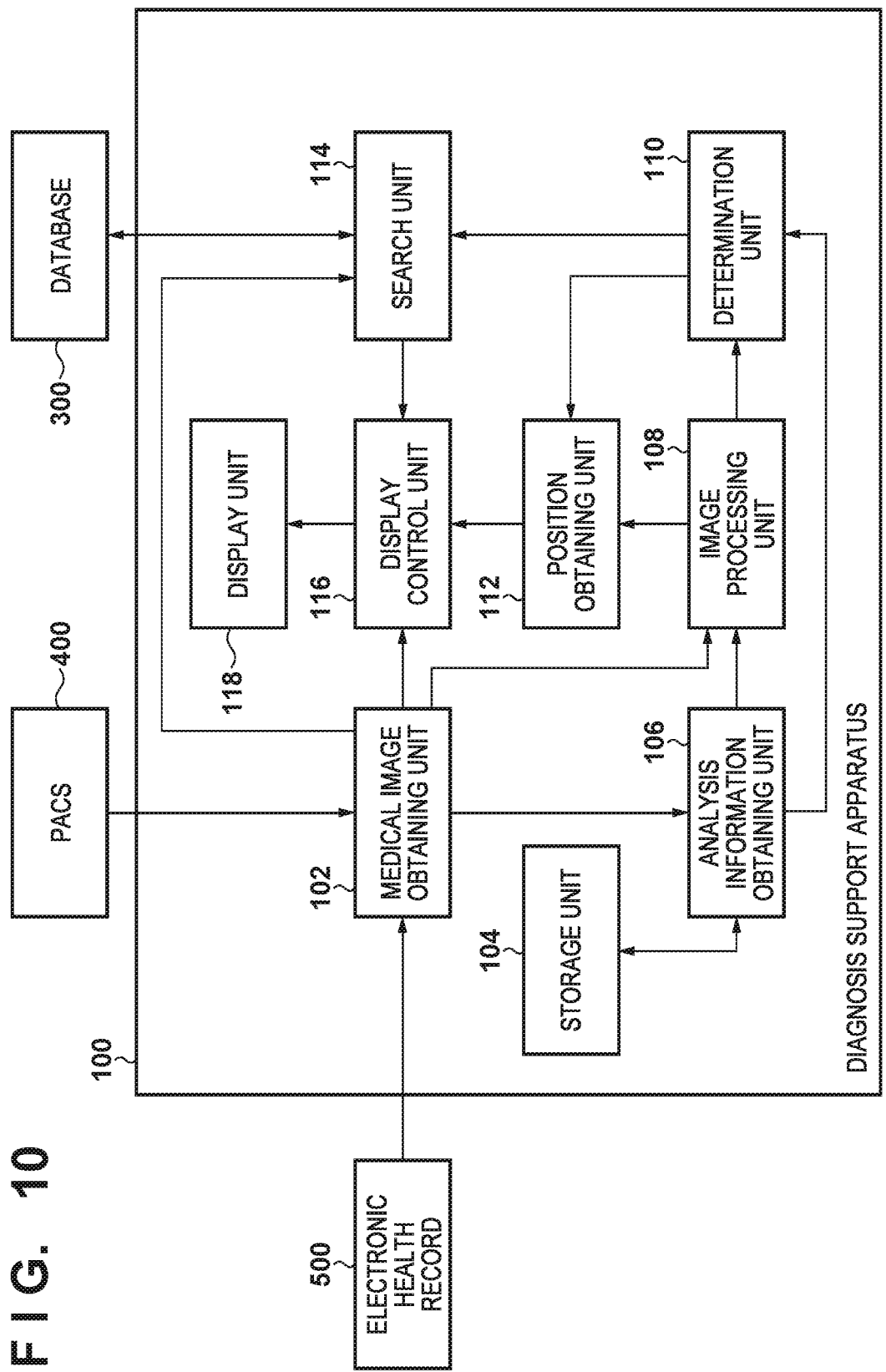
FIG. 10 is a block diagram showing another example of the functional arrangement of a diagnosis support apparatus according to the third embodiment.

FIG. 10 is a block diagram showing an example of the functional arrangement of a diagnosis support apparatus 100 according to the third embodiment. The same reference numerals as in the first embodiment (FIG. 1) denote the same constituent elements. However, the arrangements of devices connected to the diagnosis support apparatus 100 are different from those in the first embodiment. In addition, the hardware arrangement of the diagnosis support apparatus 100 according to the third embodiment is the same as that in the first embodiment (FIG. 2). That is, a CPU 1001 executes programs stored in a main memory 1002 and a magnetic disk 1003 to function as the respective functional units shown in FIG. 10. The functional arrangement of the diagnosis support apparatus 100 according to the third embodiment will be described below. As shown in FIG. 10, the diagnosis support apparatus 100 according to the third embodiment is connected to a PACS (Picture Archiving and Communication System) 400, an electronic health record 500, and a database 300.

The PACS 400 stores image data received from medical imaging apparatuses such as a CR (Computed Radiography), CT (Computed Tomography), and MRI (Magnetic Resonance Imaging). In response to a request from the diagnosis support apparatus 100, the PACS 400 outputs image data corresponding to the request to the diagnosis support apparatus 100. This image data is generally stored according to a standard called DICOM (Digital Imaging and Communications in Medicine). DICOM has information indicating the image data itself of a medical image and information called a DICOM header concerning the medical image. The DICOM header holds information concerning the type of medical image and information concerning an imaged region. That is, the diagnosis support apparatus 100 can obtain a medical image, information concerning the type of medical image, and information concerning an imaged region by obtaining a diagnosis target medical image from the PACS 400.

The electronic health record 500 stores data such as data concerning symptoms of a patient as a diagnosis target, information concerning a past clinical history, and information concerning a blood test. In this specification, these pieces of information will be generically termed clinical information. In response to a request from the diagnosis support apparatus 100, the electronic health record 500 outputs clinical information corresponding to the request to the diagnosis support apparatus 100. Obviously, a request for image data from a medical image obtaining unit 102 of the diagnosis support apparatus 100 to the PACS 400 and a request for clinical information to the electronic health record 500 originate from the same patient. Medical images, diagnosis names and findings corresponding to the images, and clinical information are linked to each other and stored as case data in the database 300. The database 300 has a data arrangement in which clinical information is linked to each case in the data arrangement shown in FIG. 5A.

The medical image obtaining unit 102 obtains, from the PACS 400, a diagnosis target medical image, information concerning the type of obtained medical image, and information concerning a region on the medical image. In addition, the medical image obtaining unit 102 obtains, from the electronic health record 500, the clinical information of the patient as the object of the medical image obtained from the PACS 400. The medical image obtaining unit 102 supplies the obtained diagnosis medical image to an image processing unit 108 and a display control unit 116, and supplies the information concerning the type of medical image and the region to an analysis information obtaining unit 106. The medical image obtaining unit 102 also supplies the clinical information to a search unit 114.

Based on a plurality of finding candidates obtained by the analysis information obtaining unit 106 and the result of image processing executed by the image processing unit 108, a determination unit 110 determines whether the plurality of finding candidates exist on the medical image (that is, correspond to it). Upon determining that a finding corresponds to the medical image, the determination unit 110 also performs quantitative determination. The determination unit 110 outputs the determination results to a position obtaining unit 112 and the search unit 114.

The search unit 114 searches the database 300 by using, as keys, the finding determined as a corresponding finding by the determination unit 110, the quantitative determination, and the clinical information obtained by the medical image obtaining unit 102, and obtains a case similar to the diagnosis target medical image. The storage unit 104, the analysis information obtaining unit 106, the image processing unit 108, the position obtaining unit 112, the display control unit 116, and a display unit 118 have the same functions as those in the first embodiment. Diagnosis support processing performed by the diagnosis support apparatus 100 according to the third embodiment having the above arrangement will be described with reference to the flowchart of FIG. 3.

In step S300, the medical image obtaining unit 102 obtains a diagnosis target medical image, information concerning the type of obtained medical image, information concerning a region on the medical image, and clinical information from the PACS 400 and the electronic health record 500. In an example in the third embodiment, the medical image obtaining unit 102 obtains a chest X-ray CT image as a diagnosis target medical image from the PACS 400. Therefore, "CT" is obtained as information concerning the type of medical image, and "chest region" is obtained as information concerning a region on the medical image. In addition, as clinical information, information concerning the chest region is obtained, including, for example, the presence/absence "cough", a clinical history concerning the lungs, and a tumor marker value (for example, CYFRA (cytokeratine 19 fragment) associated with lung cancer.

Processing in steps S301 to S303 is the same as that in the first embodiment. The following is a specific example. In the example in the third embodiment, since the region is "chest region" and the type is "CT", the analysis information obtaining unit 106 obtains a plurality of finding candidates such as an air bronchogram, a fine spiculation, and calcification from first table information 41 (FIG. 4A) in step S301. In step S302, the analysis information obtaining unit 106 obtains parameters for image processing associated with these finding candidates from second table information 42 (FIG. 4B). If a finding is "fine spiculation" and the type of image is "CT" as shown in FIG. 4B, the analysis information obtaining unit 106 obtains the image processing parameter "for nodular opacity, calculation of a distance from the barycentric position to the periphery (angular intervals of $\pi/180$)". Likewise, if a finding is "calcification" and the type of image is "CT", the analysis information obtaining unit 106 obtains the image processing parameter "for nodular opacity, extraction of a CT value: 200 HU or more".

In the third embodiment as well, the image processing unit 108 performs preprocessing for an overall diagnosis target medical image before applying an image processing parameter in step S303. More specifically, in preprocessing, the image processing unit 108 performs processing such as isotropic conversion and noise removal, and then extracts lung fields and lesion candidates in the lung fields. For example, the following technique can be applied to the extraction of lung fields: Nakagomi K et al., "Multi-shape graph cuts with neighbor prior constraints and its application to lung segmentation from a chest CT volume", Med Image Anal 17(1): 62-77, 2013 (non-patent literature 1). The following technique can be applied to the extraction of lesion candidates: Gurcan M T et al., "Lung nodule detection on thoracic computed tomography images: preliminary evaluation of a computer-aided diagnosis system", Med Phys 29(11): 2552-2558, 2002 (non-patent literature 2). The image processing unit 108 then processes the diagnosis target medical image based on image processing parameters corresponding to a plurality of finding candidates. For example, with regard to "calcification", a region with a CT value of 200 HU or more is extracted from a region estimated to be a nodular opacity by preprocessing.

In step S304, the determination unit 110 determines whether each of the plurality of finding candidates is a corresponding finding, based on the plurality of finding candidates obtained in step S302, the result of the image processing executed in step S303, and a determination criterion obtained from the second table information 42. If a given finding is determined as a corresponding finding, the determination unit 110 in the third embodiment further performs quantitative determination.

This operation will be described below by taking "calcification" as an example. First of all, if a region extracted by the image processing unit 108 according to a calcification parameter has three-dimensionally continuous nine or more pixels, the determination unit 110 determines that the region corresponds to "calcification". The determination unit 110 then calculates the occupation ratio of "calcification" based on the volume of the region estimated as a nodular opacity and the volume of the region corresponding to "calcification", and perform quantitative determination based on the calculated ratio. Such a quantitative determination may be held as the numerical value of the ratio itself, or held as a discrete determination such as "strong" if, for example, the ratio is 0.5 or more. Alternatively, a determination may be held inside as a numerical value, and a discrete determination may be made from the numerical value at the time of display and output. Assume that in this embodiment, a quantitative determination is held as a numerical value, and a discrete determination is made at the time of display. Assume that all numerical values associated with quantitative determinations of a plurality of finding candidates take positive values. Obviously, numerical values taking negative values can also be used for a quantitative determination by being converted into values taking positive values.

In step S305, based on the result of image processing executed in step S303 and the finding candidate determined as a corresponding finding in step S304, the position obtaining unit 112 obtains information indicating a position on the medical image which corresponds to the finding. This processing is the same as that in the first embodiment.

In step S306, the search unit 114 obtains a similar image from the database 300 by using, as keys, the finding determined as a corresponding key and the quantitative determination in step S304 and the clinical information obtained in step S300. That is, in the third embodiment, the search unit 114 calculates a similarity in consideration of the finding in addition to the clinical information obtained in step S300 and the quantitative determination obtained in step S304, and obtains a similar image based on the calculated similarity. Note that when calculating this similarity, the value of a quantitative determination on a finding determined not as a corresponding finding is 0. Assume that when clinical information such as information concerning cough or a clinical history takes a discrete value, a numerical value is assigned to the determination in a pseudo manner. For example, since cough takes two values: "presence" and "absence", 1 is assigned in the case of "presence", and 0 is assigned in the case of "absence". Alternatively, if clinical information takes three values, 0, 1, and 2 may be assigned. A similarity is then defined by a Mahalanobis' generalized distance using both a finding and clinical information. As the Mahalanobis' generalized distance becomes closer to 0, the two images become more similar.

Note that the quantitative determination results of findings of cases recorded on the database 300 may be calculated from medical images and findings included in the cases or may be registered in the database 300 in advance. In step S307, the display control unit 116 controls information displayed on the display unit 118. Processing in step S307 is the same as that in the first embodiment.

FIG. 11 shows display contents displayed on the display unit 118 by the display control unit 116. A display contents 1100 include a CT image 1110 as a diagnosis target medical image, a lesion candidate 1114 in the CT image 1110, and an enlarged display 1115 of the lesion candidate. The display contents 1100 also include a similar case list 1120. In addition, a CT image 1130 as a medical image of one case in the list (a case with the highest similarity based on a Mahalanobis' generalized distance) and a corresponding diagnosis name 1132 are displayed. Furthermore, the display contents 1100 include a lesion candidate 1134 in the CT image 1130 and an enlarged display 1135 of the lesion candidate.

The lesion candidates 1114 and 1134 superimposed/displayed on the CT images 1110 and 1130 are small as compared with the overall sizes of the CT images. For this reason, the display control unit 116 separately provides the enlarged displays 1115 and 1135 of the lesion candidates to allow the user to easily check the superimposed/displayed contents (lesion candidates). In this embodiment, in the enlarged displays 1115 and 1135 of the lesion candidates, the information of each finding determined as a corresponding finding is displayed based on information indicating the position of the finding in accordance with preset display rules. In addition, for example, when displaying the information of each finding, the display control unit 116 displays the quantitative determination result of each finding determined as a corresponding finding by using a discrete determination like "calcification (weak)".

As described above, according to the third embodiment, even if a medical image is a three-dimensional medical image constituted by a plurality of tomographic images, the diagnosis support apparatus 100 allows the doctor to check each finding determined as a corresponding finding and its position on the medical image, together with a diagnosis name linked to a similar image. This enables the doctor to browse the state of medical image as a current target and the diagnosis name of a similar case, thereby reducing the load of making a diagnosis.

(Modification 3-1)

In the third embodiment, in step S306, a similarity is calculated by using information obtained by unifying a finding and clinical information. However, it is also possible to calculate the respective similarities of a finding and clinical information and obtain a similar image based on a similarity obtained by unifying the respective similarities. In this instance, the similarity of a finding and the similarity of clinical information may be calculated by different methods. For example, the similarity of the finding may be calculated by a Mahalanobis' generalized distance, and the similarity of the clinical information may be calculated by a cosine similarity. In this instance, letting Sa be the overall similarity, Sf be the similarity of the finding, and Sc be the similarity of the clinical information, the overall similarity Sa can be defined by, for example, $$Sa=(1-\alpha)Sf+\alpha(1-Sc) \quad (2)$$

In the above equation, $\alpha(0\leq\alpha\leq1)$ is a coefficient for determining to which one of the similarity of the finding and the similarity of the clinical information a higher importance should be placed. That is, as $\alpha$ becomes closer to 0, a higher importance is placed on the similarity of the finding, whereas as $\alpha$ becomes closer to 1, a high importance is placed on the similarity of the clinical information. In addition, as Sf is closer to 0, it indicates a higher similarity, whereas as (1−Sc) is closer to 0, it indicates a higher similarity. Therefore, as Sa is closer to 0, it indicates a higher similarity. Obviously, it is possible to use another method of calculating a similarity by unifying the two types of similarities.

(Modification 3-2)

In third embodiment, the display contents displayed by the display unit 118 in step S307 have the information of all findings determined as corresponding findings superimposed/displayed on the enlarged displays of the lesion candidates in the CT images. However, this is not exhaustive. For example, the user may be allowed to arbitrarily designate an enlargement ratio of an enlarged display of a lesion candidate, and the information of findings to be superimposed/displayed may be changed in accordance with a designated enlargement ratio. More specifically, it is possible to present only the information of a finding determined as a finding which can be recognized at a designated enlargement ratio. Whether it is possible to recognize a finding at a designated enlargement ratio can be performed based on the relationship between the size (area) of a region to which the finding corresponds. For example, if the result obtained by multiplying the size of a region to which a finding corresponds by an enlargement ratio is larger than a predetermined area value, the finding may be set as a target to be superimposed/displayed on an enlarged display.

Other Embodiments

All or some of these functions may be arranged on a network. In this instance, a server-client type arrangement may be adopted, in which only the display function or some functions are made to operate on the local side. In addition, for example, the diagnosis support apparatus 100 may be implemented by a tablet type computer (tablet PC) having a touch panel. Alternatively, the diagnosis support apparatus 100 may be constituted by a monitor having a touch panel and a computer (stick type PC) connected to the HDMI® terminal of the monitor.

As described above, according to the above embodiments, findings detected from a diagnosis target medical image are presented, and a similar case obtained based on the detected findings is also presented. This allows the user (doctor) to more easily determine the appropriateness of a similar case, and hence reduces the load associated with a diagnosis.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-099514, filed May 14, 2015 which is hereby incorporated by reference herein in its entirety.

What is claimed is:

1. A diagnosis support apparatus, comprising:
a detection unit configured to detect, from a diagnosis image, a finding and a position corresponding to the finding on the diagnosis image by performing image processing on the diagnosis image, wherein the finding is a text description that expresses a state of an object;
a search unit configured to search a database storing a plurality of medical images associated with findings and diagnosis names for a medical image using the finding detected by the detection unit; and
a display control unit configured to perform first and second display operations, said first display operation causing a display unit to display a first composite image obtained by superimposing, on the diagnosis image, the finding detected by the detection unit and a first marker, wherein the finding detected by the detection unit and the first marker are arranged at a display position, inside a display region of the diagnosis image, corresponding to the position of the finding detected by the detection unit, and said second display operation causing the display unit to display a second composite image obtained by superimposing, on a medical image searched for by the search unit, a finding associated with the searched-for medical image and a second marker together with a diagnosis name associated with the searched-for medical image, wherein the finding associated with the searched-for medical image and the second marker are arranged at a display portion, inside a display region of the searched-for medical image, corresponding to a position of the finding associated with the searched-for medical image.

2. The apparatus according to claim 1, wherein the display control unit is configured to cause the display unit to display a list of the searched-for medical image(s).

3. The apparatus according to claim 2, wherein, in the second display operation, selection of a medical image from the list by a user is accepted, and the selected searched-for medical image is used to display the second composite image.

4. The apparatus according to claim 1, wherein the detection unit comprises:
an obtaining unit configured to obtain finding candidates associated with the diagnosis image by referring to first table information associating a region of an object included in a medical image or a type of medical image with a finding candidate; and
a determination unit configured to determine a finding, from finding candidates obtained by the obtaining unit, which exists in the diagnosis image.

5. The apparatus according to claim 4, wherein the determination unit is configured to obtain parameters respectively corresponding to finding candidates obtained by the obtaining unit by referring to second table information associating finding candidates with parameters for image processing for detection of the finding candidates, and
to determine whether the finding candidates exist in the diagnosis image by processing the diagnosis image using obtained parameters.

6. The apparatus according to claim 1, wherein the database stores an image set including a plurality of medical images of one object region in a plurality of directions, which are associated with a finding and a diagnosis name,
the detection unit is configured to detect a finding and a position of the finding with respect to at least one of a plurality of diagnosis images of one object region obtained in the plurality of directions,
the search unit is configured to search the database for an image set based on the finding detected by the detection unit, and
the display control unit is configured to perform the first display operation by using at least one of the plurality of diagnosis images and perform the second display operation by using at least one medical image included in the image set searched for by the search unit.

7. The apparatus according to claim 6, wherein the search unit is configured to perform a search by comparing a finding detected from one of the plurality of diagnosis images with a finding associated with a medical image corresponding to a direction of the one diagnosis image of the plurality of medical images included in the image set.

8. The apparatus according to claim 6, wherein the search unit is configured to perform a search by comparing a finding detected from a diagnosis image, of the plurality of diagnosis images, which is obtained in one direction with a finding associated with medical image in each direction stored in the database.

9. The apparatus according to claim 6, wherein the search unit is configured to perform a search by comparing a finding detected from each of the plurality of diagnosis images with a finding associated with each of a plurality of images included in the image set.

10. The apparatus according to claim 1, wherein the search unit is configured to perform a search by using clinical information associated with the diagnosis image and clinical information associated with an object of the diagnosis image.

11. The apparatus according to claim 10, wherein the search unit is configured to obtain the clinical information from an electronic health record of an object of the diagnosis image.

12. The apparatus according to claim 1, wherein the detection unit is configured to perform a quantitative determination with respect to the finding determined as existing in the diagnosis image, and
the search unit is configured to search the database by further using a result of a quantitative determination with respect to the finding detected by the detection unit.

13. The apparatus according to claim 1, wherein the display control unit is configured to generate an enlarged display of the diagnosis image or the searched-for medical image at an enlargement ratio designated by a user, and the first or second display operation displays the first or second composite image by superimposing, on the enlarged display, a finding, of the findings detected by the detection unit, whose area value exceeds a predetermined area value at the enlargement ratio.

14. The apparatus according to claim 1, further comprising a storage unit configured to store a partial database extracted from the database based on a condition, wherein
the search unit is configured to search the partial database stored in the storage unit.

15. A control method for a diagnosis support apparatus, the method comprising:
detecting, from a diagnosis image, a finding and a position corresponding to the finding on the diagnosis image by performing image processing on the diagnosis image, wherein the finding is a text description that expresses a state of an object;
searching a database storing a plurality of medical images associated with findings and diagnosis names by using the detected finding; and
performing first and second display operations, said first display operation causing a display unit to display a first composite image obtained by superimposing, on the diagnosis image, the detected finding and a first marker, wherein the detected finding and the first marker are arranged at a display position, inside a display region of the diagnosis image, corresponding to the position of the detected finding, and said second display operation causing the display unit to display a second composite image obtained by superimposing, on a medical image searched for by the search unit, a finding associated with the searched-for medical image and a second marker, together with a diagnosis name associated with the medical image, wherein the finding associated with the searched-for medical image and the second marker are arranged at a display position, inside a display region of the searched-for medical issue, corresponding to a position of the finding associated with the searched-for medical image.

16. A non-transitory computer-readable storage medium storing a program for causing a computer to execute a control method for a diagnosis support apparatus, the control method comprising:
detecting, from a diagnosis image, a finding and a position corresponding to the finding on the diagnosis image by performing image processing on the diagnosis image, wherein the finding is a text description that expresses a state of an object;
searching a database storing a plurality of medical images associated with findings and diagnosis names by using the detected finding; and
performing first and second display operations, said first display operation causing a display unit to display a first composite image obtained by superimposing, on the diagnosis image, the detected finding and a first marker, wherein the detected finding and the first marker are arranged at a display position, inside a display region of the diagnosis image, corresponding to the position of the detected finding, and said second display operation causing the display unit to display a second composite image obtained by superimposing, on a medical image searched for by the search unit, a finding associated with the searched-for medical image and a second marker, together with a diagnosis name associated with the medical image, wherein the finding associated with the searched-for medical image and the second marker are arranged at a display position, inside a display region of the searched-for medical issue, corresponding to a position of the finding associated with the searched-for medical image.

17. The apparatus according to claim 1, wherein the display control unit is configured to perform the second display operation based on a degree of similarity between the medical image searched for by the search unit and the diagnosis image.

18. The apparatus according to claim 17, wherein the display control unit is configured to perform the second display operation based on the degree of similarity between each of a plurality of medical images searched by the search unit and the diagnosis image.

19. The apparatus according to claim 17, wherein the display control unit is configured to perform, based on a plurality of medical images searched by the search unit, the second display operation in descending order of the degree of similarity.

20. The apparatus according to claim 1, wherein the search unit is configured to search a medical image similar to the diagnosis image, from a plurality of medical images stored in the database, based on a degree of coincidence between the finding detected by the detection unit and a finding associated with the medical image stored in the database.

21. The apparatus according to claim 1, wherein the search unit is configured to search, from a plurality of medical images stored in the database, for a medical image in which a finding detected by the detection unit and a finding associated with the medical image stored in the database coincide.

22. The apparatus according to claim 1, further comprising an adding unit configured to add, to the database searched by the searching unit, the diagnostic image and a finding detected from the diagnostic image displayed on the display unit by the first display operation.

23. The apparatus according to claim 1, wherein the first display operation does not include a display of a diagnosis name.

24. A diagnosis support apparatus, comprising:
an obtaining unit configured to obtain a candidate of a finding that may exist in a part of an object in a diagnostic image, wherein the finding is a text description that expresses a state of an object;
a detection unit configured to detect, from the candidate of a finding, a finding which is included in the diagnosis image, and a position corresponding to that finding on the diagnosis image by performing image processing on the diagnosis image;
a search unit configured to search a database storing a plurality of medical images associated with findings and diagnosis names for an image similar to the diagnosis image by using the detected finding; and
a display control unit configured to perform first and second display operations, said first display operation causing a display unit to display a first composite image obtained by superimposing, on the diagnosis image, the detected finding and a first marker, wherein the finding detected by the detection unit and the first marker are arranged at a display position, inside a display region of the diagnosis image, corresponding to the position of the finding detected by the detection unit, and said second display operation causing the display unit to display a second composite image obtained by superimposing, on the similar image searched for by the search unit, a finding associated with the searched-for similar image, and a second marker together with the diagnosis name associated with the searched-for medical image, wherein the finding associated with the searched-for medical image and the second marker are arranged at a display portion, inside a display region of the searched-for medical image, corresponding to a position of the finding associated with the searched-for medical image.

25. A diagnosis support apparatus, comprising:
a detection unit configured to detect, from a diagnosis image, a finding that is a text description expressing state of lesion of an object and a position of the lesion expressed by the finding on the diagnosis image by performing image processing on the diagnosis image;
a search unit configured to search a database storing a plurality of medical images associated with findings and diagnosis names for a medical image by using the finding detected by the detection unit; and
a display control unit configured to perform first and second display operations, said first display operation causing a display unit to display a first composite image obtained by superimposing, on the diagnosis image, the finding and a first marker, wherein the finding detected by the detection unit and the first marker are arranged at a display portion, inside a display region of the diagnosis image, corresponding to the position of the finding detected and said second display operation causing the display unit to display a second composite image obtained by superimposing, on the searched-for medical image, a finding associated with the searched-for medical image and a second marker, together with a diagnosis name associated with the searched-for medical image, wherein the finding associated with the searched-for medical image and the second marker are arranged at a display portion, inside a display region of the searched-for medical image, corresponding to a position of the finding associated with the searched-for medical image.

26. A diagnosis support system, comprising:
a detection unit configured to detect, from a diagnosis image, a finding and a position corresponding to the finding on the diagnosis image by performing image processing on the diagnosis image, wherein the finding is a text description expressing state of an object;
a search unit configured to search a database storing a plurality of medical images associated with findings and diagnosis names for a medical image by using the finding detected by the detection unit; and
a display control unit configured to perform first and second display operations, said first display operation causing a display unit to display a first composite image obtained by superimposing, on the diagnosis image, the finding detected by the detection unit and a first marker, wherein the finding detected by the detection unit and the first marker are arranged at a display position, inside a display region of the diagnosis image, corresponding to the position of the finding detected by the detection unit, and said second display operation causing the display unit to display the second composite image obtained by superimposing, on the medical image searched for by the search unit, a finding associated with the searched-for medical image and a second marker, together with the diagnosis name associated with the searched-for medical image, wherein
the finding associated with the searched-for medical image and the second marker are arranged at a display portion, inside a display region of the searched-for medical image, corresponding to a position of the finding associated with the searched-for medical image.

27. A diagnosis support apparatus, comprising:
a detection unit configured to detect, from a diagnosis image, a plurality of findings and positions corresponding to the plurality of findings on the diagnosis image by performing image processing on the diagnosis image, wherein the findings are a text description that expresses a state of an object;
a search unit configured to search a database storing a plurality of medical images associated with findings and diagnosis names for a medical image using the plurality of findings detected by the detection unit; and
a display control unit configured to perform first and second display operations, said first display operation causing a display unit to display a first composite image obtained by superimposing, on the diagnosis image, the plurality of findings detected by the detection unit and a first markers, wherein the plurality of findings detected by the detection unit and the first markers are arranged at a display positions, inside a display region of the diagnosis image, corresponding the positions of the plurality of findings detected by the detection unit and
said second display operation causing the display unit to display a second composite image obtained by superimposing, on a medical image searched for by the search unit, a findings associated with the searched-for medical image and a second markers together with a diagnosis name associated with the searched-for medical image, wherein the findings associated with the searched-for medical image and the second markers are arranged at a display positions, inside a display region of the searched-for medical image, corresponding to a positions of the findings associated with the searched-for medical image.

\* \* \* \* \*